United States Patent
Eck et al.

(10) Patent No.: US 8,470,576 B2
(45) Date of Patent: Jun. 25, 2013

(54) GROUP OF NOVEL ENANTIOSELECTIVE MICROBIAL NITRILE HYDRATASES WITH BROAD SUBSTRATE SPECIFICITY

(75) Inventors: Jürgen Eck, Bensheim (DE); Klaus Liebeton, Zwingenberg (DE); Lutz Fischer, Stuttgart (DE); Sabine Lutz-Wahl, Kirchheim/Teck (DE); Martina Hensel, Beitigheim-Bissingen (DE); Christian Ewert, Weingarten (DE); Marcus Wälz, Stuttgart (DE)

(73) Assignee: B.R.A.I.N. AG, Zwingenberg (DE)

( * ) Notice: Subject to any disclaimer, the term of this patent is extended or adjusted under 35 U.S.C. 154(b) by 842 days.

(21) Appl. No.: 12/296,057

(22) PCT Filed: Apr. 5, 2007

(86) PCT No.: PCT/EP2007/003114
§ 371 (c)(1),
(2), (4) Date: Nov. 6, 2009

(87) PCT Pub. No.: WO2007/115797
PCT Pub. Date: Oct. 18, 2007

(65) Prior Publication Data
US 2010/0047863 A1    Feb. 25, 2010

(30) Foreign Application Priority Data
Apr. 7, 2006  (EP) .................................... 06007383

(51) Int. Cl.
| C12N 9/78 | (2006.01) |
| C12N 15/00 | (2006.01) |
| C12N 1/20 | (2006.01) |
| C12P 21/06 | (2006.01) |
| C12P 21/04 | (2006.01) |
| C12Q 1/68 | (2006.01) |
| C07H 21/04 | (2006.01) |

(52) U.S. Cl.
USPC .......... 435/227; 435/6.1; 435/69.1; 435/71.1; 435/252.3; 435/320.1; 435/440; 536/23.2

(58) Field of Classification Search
USPC ................................ 435/227, 252.3; 536/23.2
See application file for complete search history.

(56) References Cited

U.S. PATENT DOCUMENTS
5,811,286 A * 9/1998 Fallon et al. ............... 435/252.3
2004/0014195 A1    1/2004 DeSantis et al. ............... 435/228

FOREIGN PATENT DOCUMENTS
| JP | 06-303971 | * | 1/1994 |
| JP | 06303971 | | 1/1994 |
| WO | 02/29079 A2 | | 4/2002 |
| WO | 2005/090595 A2 | | 9/2005 |

OTHER PUBLICATIONS

Branden et al. Introduction to Protein Structure, Garland Publishing Inc., New York, p. 247, 1991.*
Machine Translation of JP 06-303971. Retrived from the internet via http://www4.ipdl.inpit.go.jp/Tokujitu/PAJdetail.ipdl?N0000=60 &N0120=01&N2001=2&N3001=H06-303971 on Sep. 25, 2012.*
Brady, D., et al., Characterisation of Nitrilase and Nitrile Hydratase Biocatalytic Systems, Appl. Microbiol. Biotechnol., 64:76-85 (2004).
Payne, Mark S., et al., A Stereoselective Cobalt-Containing Nitrile Hydratase, Biochemistry, 36:5447-5454 (1997).
Robertson, Dan E., et al., Exploring Nitrilase Sequence Space for Enantioselective Catalysis, Applied and Environmental Microbiology, 70(4):2429-2436 (2004).

* cited by examiner

*Primary Examiner* — Yong Pak
(74) *Attorney, Agent, or Firm* — Pillsbury Winthrop Shaw Pittman LLP

(57) ABSTRACT

The present invention provides a polynucleotide or a pair of polynucleotides encoding an enzyme having nitrile hydratase (NHase) [E.C. 4.2.1.84] activity. Furthermore, a vector and a host comprising the disclosed polynucleotide or pair of polynucleotides and methods for the production of the same are provided. Moreover, the invention relates to a pair of polypeptides or a fusion protein having NHase activity, an antibody specifically binding to the pair of polypeptides or fusion protein, a primer or probe, which specifically hybridizes under stringent conditions to the disclosed polynucleotide or either one of the pair of polynucleotides, a composition comprising the polynucleotide or pair of polynucleotides, the pair of polypeptides or fusion protein, the antibody and/or one or more primers or probes of the invention and a method for the production of amides comprising the enantioselective conversion of nitriles.

10 Claims, 9 Drawing Sheets

Figure 24:
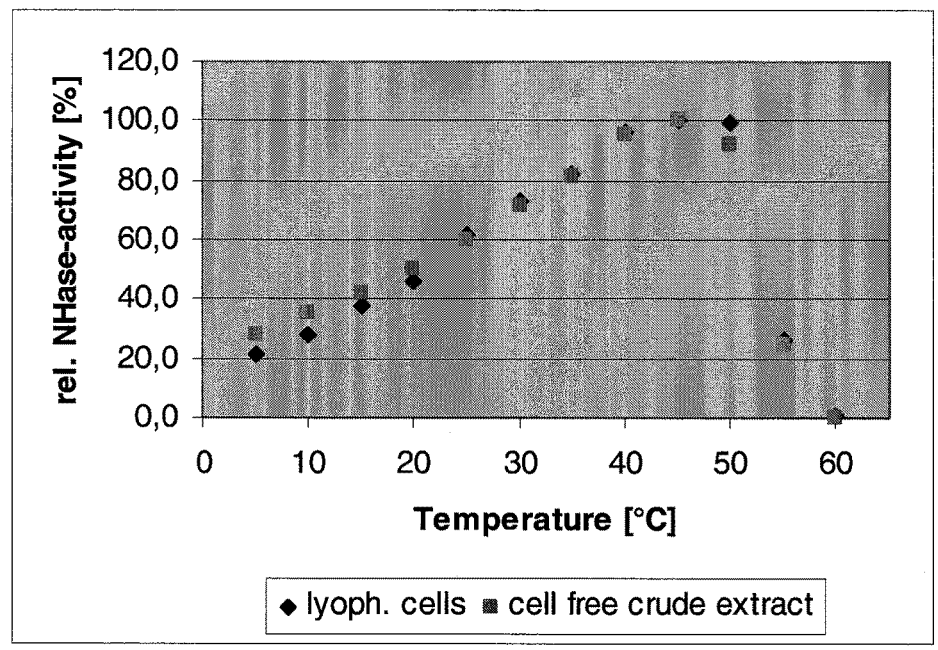

Figure 1: Seq ID No. 1 (*Raoultella terrigena*, strain 77.1) α-subunit

ATGAGCCATAAACACGACCACGACCACACCGAACCACCAGTAGACATCGAGTTACGTGTCCGC
GCACTGGAATCCCTGCTACAGGAAAAAGGACTAATCGACCCGGCGGCTCTGGATGAGTTGATT
GACACCTATGAGCACAAAGTCGGCCCGCGCAATGGCGCACAGGTTGTCGCCAGAGCGTGGAGC
GACCCGGAATACAAACGTCGACTGATGGAAAACGCCACCGCCGCCATCTCAGAACTGGGTTTC
TCCGGTATACAGGGCGAAGACATGTTGGTGGTTGAGAACACGCCGGACGTGCACAACGTCACC
GTCTGCACGCTGTGCTCCTGCTACCCCTGGCCGGTACTGGGTCTGCCACCTGTCTGGTACAAA
TCAGCCCCCTATCGTTCGCGTATTGTCATCGACCCACGCGGCGTTCTGGCCGAGTTCGGGTTA
CACATTCCCGAAAGCAAAGAGATTCGCGTCTGGGACAGCAGCGCCGAGTTGCGTTATCTGGTA
CTGCCTGAACGTCCGGCGGGCACAGACGGCTGGAGCGAAGCGCAGTTGAGCGAACTGATCTCG
CGCGATTCGATGATTGGCACCGGTGTGGTTACCGCACCATAA

Figure 2: Seq ID No. 2 (Raoultella terrigena, strain 77.1) α-subunit

MSHKHDHDHTEPPVDIELRVRALESLLQEKGLIDPAALDELIDTYEHKVGPRNGAQVVARAWS
DPEYKRRLMENATAAISELGFSGIQGEDMLVVENTPDVHNVTVCTLCSCYPWPVLGLPPVWYK
SAPYRSRIVIDPRGVLAEFGLHIPESKEIRVWDSSAELRYLVLPERPAGTDGWSEAQLSELIS
RDSMIGTGVVTAP

Figure 3 Seq ID No. 3 (Raoultella terrigena, strain 77.1) β-subunit

ATGAACGGGATACACGATCTCGGCGGTATGCACGGCTTCGGCCCGATCCCTACCGAGGAAAAC
GAGCCCTATTTCCACCATGAGTGGGAGCGCCGGGTCTTTCCAATGTTCGCCTCGTTGTTTGTC
GGCGTACACTTTAACGTCGACGAATTTCGCCATTCCATCGAATGTATGCCCCCTGCCGACTAT
CTGCAGTCGAGTTACTACGAGCACTGGCTGCATGCATTCGAAACCCTGCTGCTGGCAAAGGGG
GTGATCACCGTTGACGAGTTGTGGGGTGGCGCGAAGCCCACCCTCTGTAAGCCAGGCACACCT
GTGCTGACGCAGGACATGGTATCGATGGTCGTCAGCACCGGCGGCTCTGCTCGCGTCAGTCAC
GACGTTGCGCCCCGCTTCCGGGTGGGAGATCGGGTACGAACGAAAAATTTCAACCCGACCACC
CATACCCGTCTGCCGCGTTACGCACGCGATAAAGTCGGCCGCATAGAAATTGCTCACGGTGTG
TTTATCACGCCAGATACCGCGGCGCATGGCCTGGGCGAACATCCCCAGCATGTCTACAGCGTC
AGTTTCACCGCGCAGGAGCTGTGGGGGGAACCACGCCCGGACAACGTGTTCATCGATCTGTGG
GACGACTATCTGGAGGAAGCATGA

Figure 4 Seq ID No. 4 (Raoultella terrigena, strain 77.1) β-subunit

MNGIHDLGGMHGFGPIPTEENEPYFHHEWERRVFPMFASLFVGVHFNVDEFRHSIECMPPADY
LQSSYYEHWLHAFETLLLAKGVITVDELWGGAKPTLCKPGTPVLTQDMVSMVVSTGGSARVSH
DVAPRFRVGDRVRTKNFNPTTHTRLPRYARDKVGRIEIAHGVFITPDTAAHGLGEHPQHVYSV
SFTAQELWGEPRPDNVFIDLWDDYLEEA

Figure 5 Seq ID No. 5 (Raoultella terrigena, strain 37.1) α-subunit

ATGAGCCATAAACACGACCACGACCACACCGAACCACCAATAGACATCGAGTTACGTGTCCGC
GCACTGGAATCCCTGCTACAGGAAAAAGGACTAATCGACCCTGCGGCTCTGGATGAGTTGATT
GACACCTATGAGCACAAAGTCGGCCCGCGCAATGGCGCACAGGTTGTCGCCAGAGCGTGGAGC
GACCCGGAATACAAACGTCGACTGATGGAAAACGCCACCGCCGCCATCTCAGAACTGGGTTTC
TCCGGTATACAGGGCGAAGACATGTTGGTGGTTGAGAATACGCCGGACGTGCACAACGTGACC
GTCTGTACGCTGTGCTCCTGCTACCCCTGGCCGGTACTGGGTCTGCCACCTGTCTGGTACAAA
TCAGCACCCTATCGTTCGCGTATTGTCATCGACCCACGCGGCGTTCTGGCCGAGTTCGGGTTA
CACATTCCCGAAAGCAAAGAGATTCGCGTCTGGGACAGCAGCGCCGAGTTGCGTTATCTGGTA
CTGCCTGAACGTCCGGCGGGTACAGACGGCTGGAGCGAAGCGCAGTTGAGCGAACTGATCTCG
CGCGATTCGATGATTGGCACCGGTGTGGTTACCGCACCATAA

Figure 6 Seq ID No. 6 (Raoultella terrigena, strain 37.1) α-subunit

MSHKHDHDHTEPPIDIELRVRALESLLQEKGLIDPAALDELIDTYEHKVGPRNGAQVVARAWS
DPEYKRRLMENATAAISELGFSGIQGEDMLVVENTPDVHNVTVCTLCSCYPWPVLGLPPVWYK
SAPYRSRIVIDPRGVLAEFGLHIPESKEIRVWDSSAELRYLVLPERPAGTDGWSEAQLSELIS
RDSMIGTGVVTAP

Figure 7 Seq ID No. 7 (Raoultella terrigena, strain 37.1) β-subunit

ATGAACGGGATACACGATCTCGGCGGTATGCACGGCTTCGGCCCGATCCCTACCGAGGAAAAT
GAGCCCTATTTCCACCATGAGTGGGAGCGCCGGGTATTTCCAATGTTCGCCTCGTTGTTTGTC
GGCGGACACTTCAACGTCGACGAATTTCGCCATTCCATCGAATGTATGCCTCCTGCCGACTAT
CTGCAGTCGAGTTACTACGAGCACTGGCTGCATGCATTCGAAACCCTGCTGCTGGCAAAGGGG
GTGATCACCGTTGACGAGTTGTGGGGTGGCGCGAAGCCTACCCTCTGTAAGCCTGGCACACCT
GTGCTGACGCAGGACATGGTATCGATGGTCGTCAGCACCGGCGGCTCTGCTCGCGTCAGTCAC
GACGTTGCGCCCCGCTTCCGGGTGGGAGATCGGGTACGAACGAAAAATTTCAACCCGACCACC
CATACCCGTCTGCCCCGTTACGCACGCGATAAAGTCGGCCGCATAGAAATTGCTCACGGTGTG
TTTATCACGCCAGATACCGCGGCGCACGGCCTGGGCGAACATCCCCAGCATGTCTACAGCGTC
AGTTTCACCGCGCAGGAGCTGTGGGGGGAACCACGCCCGGACAACGTGTTCATCGATCTGTGG
GACGACTATCTGGAGGAAGCATGA

Figure 8 Seq ID No. 8 (Raoultella terrigena, strain 37.1) β-subunit

MNGIHDLGGMHGFGPIPTEENEPYFHHEWERRVFPMFASLFVGGHFNVDEFRHSIECMPPADY
LQSSYYEHWLHAFETLLLAKGVITVDELWGGAKPTLCKPGTPVLTQDMVSMVVSTGGSARVSH
DVAPRFRVGDRVRTKNFNPTTHTRLPRYARDKVGRIEIAHGVFITPDTAAHGLGEHPQHVYSV
SFTAQELWGEPRPDNVFIDLWDDYLEEA

Figure 9 Seq ID No. 9 (Pantoea sp., strain 17.3.1) α-subunit

ATGTCAAATCATGATGTCTTACCTTCCGAAAGTGCCCTCAAAGTGCGGGCGATTCAGTCACTC
CTGACGGAGAAAGGTTTGCTCGATCCACAAACTTCAGACGCCATCGTGGACTATTTTGAAAAC
AAAATCGGTCCCCGCAACGGTGCAAGTGTCGTGGCGCGTGCCTGGCTTGATGCCGAATTCAAA
AAGAAGCTGCTTGAAGATGGCACTACTGCCATCAGCGAGATGGGGTTCTCAGGTGCCGAAGGC
GCAGTCATTCACGTGCTCGAAAACACTGATGCGGTGCATAACATCGTCGTTTGTACGCTGTGC
TCCTGTTATCCGTGGCCGGTACTGGGGTTACCGCCAATCTGGTTTAAGTCTGCACAGTACCGC
TCCCGTGTGGTGATTGATCCAAGAGGCGTGCTGAAGGAGTTCGGTACTGAGCTTCCACCTGAG
AAAGAGATTCGCGTATGGGACAGCAATGCCGAAATCCGCTATTTCGTATTGCCGCAACGCCCG
GCGGGCACGGAGAACCTGAGTGAAGAACAACTGGCCGCGAGAGTGACCCGCGATTCAATGATT
GGTACGGGCATCCTTTAA

Figure 10 Seq ID No. 10 (Pantoea sp., strain 17.3.1) α-subunit

MSNHDVLPSESALKVRAIQSLLTEKGLLDPQTSDAIVDYFENKIGPRNGASVVARAWLDAEFK
KKLLEDGTTAISEMGFSGAEGAVIHVLENTDAVHNIVVCTLCSCYPWPVLGLPPIWFKSAQYR
SRVVIDPRGVLKEFGTELPPEKEIRVWDSNAEIRYFVLPQRPAGTENLSEEQLAARVTRDSMI
GTGIL

Figure 11 Seq ID No. 11 (Pantoea sp., strain 17.3.1) β-subunit

ATGAACGGTATACACGATTGTGGAGGAATGCAGAATCTCGGCGCTATTCCTCTGGAAGAGAAC
GAACCGGTTTTTCATGCCGAATGGGAAAAAGCGATTTTGGTGATGACCATTAACGGTTTTCTC
AGCGGGAGCATCCTGGTGGACAACTTCAGGCACCAAATTGAAAAAATGCCAGCCAGCGAATAT
CTGCTCACCTCCTATTACGAACACTGGGTTTTTGCCATGGAACATCTACTCATCAATAACAAC
ACGATTACCCGTGAAGCATTGGAATCCAGAATGGCTGAACTGGCAGAGAGAGTTGAAATGAGC
GCGATAGCTAAAGAGACCTTCCTGGAGTTGATTAAAACCACGCCAAACTACCATCGTGAAAGT
GATGCGATAGCGCGGTTTGCGCCAGGCGATACCATTCGTACCTGCGAACTGAACACGCCGGGT
CATACGCGTTTGCCGCGTTATGCACGCGATAAGACAGGAGTAATTATCGCCATGTATGGCGTG
TGTGTTTTTCCGGACTCACTGACGCGTGACGGAAGTGAAGACCCGCAGCACGTTTATCTGGTG
CAGTTCTCGTCAGCCGATCTTTGGGGGCTGGCTCAGAACCATTTACTGTCAGCTTGAGCCTG
TTCGAAAGTTATATTGCTGAGAAAGTGGAGTAA

Figure 12 Seq ID No. 12 (Pantoea sp., strain 17.3.1) β-subunit

MNGIHDCGGMQNLGAIPLEENEPVFHAEWEKAILVMTINGFLSGSILVDNFRHQIEKMPASEY
LLTSYYEHWVFAMEHLLINNNTITREALESRMAELAERVEMSAIAKETFLELIKTTPNYHRES
DAIARFAPGDTIRTCELNTPGHTRLPRYARDKTGVIIAMYGVCVFPDSLTRDGSEDPQHVYLV
QFSSADLWGAGSEPFTVSLSLFESYIAEKVE

Figure 13    Seq ID No. 13 (Brevibacterium linens, strain 32B.1) α-subunit

ATGAGCGACAAGATACGCAGCCAAGAAGAGATCGCAGCTCGGGTCAAAGCACTGGAATCGATG
CTGATCGAGAAGGGCATCATGACCACTCAAGCCATCGACAGACTGGTGGAGATCTACGAGAAC
GAAGTCGGACCTCAGCTCGGGGCGAAGGTCGTCGCCAAGGCGTGGTCGGATCCGGGATTCAAA
TCCAGACTTCTCACCGACGCAACAGGTGCCTGCGGCGAACTCGGTATCGGCGGCCTCCAGGGT
GAAGACATGGTCGTCGTGGAAGACACCGACACCGTCCACAACGTCATCGTCTGCACCTTGTGT
TCGTGCTACCCGTGGCCGGTTCTCGGGCTTCCCCCGAACTGGTACAAGGACCCGCAGTACCGG
GCCGCGATCTGCCGCGAACCCCGCAAAGTCCTCTCCGAAAGCTTCGGATACACCGTCTCCAAT
GACGTCGAGATCCGAGTCTGGGACTCCAGCAGCGAAATGCGGTACTGGGTCCTGCCCCGACGC
CCAGACGGAACCGACGGATGGACCGAAGACCAACTCGCTGATCTGGTCAGCCGCGACTCCATG
ATCGGCGTCGGCCCCACCGCGAAGGCGCAGTCATGA

Figure 14    Seq ID No. 14 (Brevibacterium linens, strain 32B.1) α-subunit

MSDKIRSQEEIAARVKALESMLIEKGIMTTQAIDRLVEIYENEVGPQLGAKVVAKAWSDPGFK
SRLLTDATGACGELGIGGLQGEDMVVVEDTDTVHNVIVCTLCSCYPWPVLGLPPNWYKDPQYR
AAICREPRKVLSESFGYTVSNDVEIRVWDSSSEMRYWVLPRRPDGTDGWTEDQLADLVSRDSM
IGVGPTAKAQS

Figure 15    Seq ID No. 15 (Brevibacterium linens, strain 32B.1) β-subunit

ATGAACGGAGTTTTCGACCTGGCCGGGACCGACGGTCTGGGTCCGGTCGTTGTCCCCGACGAC
GAGCCAATCTTCCGCGCGGAATGGGAGAAAGCCGCGTTCGGCATGTTCTCGATGTGCTTTCGC
GGCGGCTTTTTCGGCGTCGACCAGTTTCGGTACGGCATGGAACAGATCGACCCCGCCGTCTAC
CTCAAATCGCCGTACTACGAGCACTGGATCCACACCGTCGAGTACCACGGCGAACGCACCGGT
CAACTCGACCTCGACGAACTCGACCGCAGAACCGAGTACTACCTGGCCAACCCGGACGCACCG
ATGCCCGAACACGCCGACGACCCAGAACTACTAGCGTTCATCAACGCCGTCGTTCCAGCCGGT
GCACCGGCCAAACGCGAAAGCGACAAGATCGCCCGCTTTCAAGTCGGCGACACGGTGAAAGTT
CTGCGCGACTCGCCCCGCGGTCACACCCGGCGCGCCCGTTACATCCGCGGCGCGACCGGTGAA
ATCGTGCTGGCACACGGCACGTTCATCTACCCAGACACCGCAGGCAACAACCTCGGTGAATGT
CCGGAACACGTCTACACCGTCCGCTTTACAGCCGAAGAACTCTGGGGCGCAGAGACAGCCGAG
CCCAACCAATCCGTCTACTTCGACGTCTGGGACCCCTACATCGAACTCGTCACACCCCGAGGA
GCACAGTCAGCATGA

Figure 16    Seq ID No. 16 (Brevibacterium linens, strain 32B.1) β-subunit

MNGVFDLAGTDGLGPVVVPDDEPIFRAEWEKAAFGMFSMCFRGGFFGVDQFRYGMEQIDPAVY
LKSPYYEHWIHTVEYHGERTGQLDLDELDRRTEYYLANPDAPMPEHADDPELLAFINAVVPAG
APAKRESDKIARFQVGDTVKVLRDSPRGHTRRARYIRGATGEIVLAHGTFIYPDTAGNNLGEC
PEHVYTVRFTAEELWGAETAEPNQSVYFDVWDPYIELVTPRGAQSA

Figure 17    Seq ID No. 17 (Klebsiella oxytoca, strain 38.1.2) α-subunit

ATGAGCCATAAACACGACCACGACCATACCCAACCCCCCGTTGATATCGAGCTACGCGTCCGC
GCACTGGAATCCCTGCTGCAGGAAAAAGGCCTGATCGACCCGGCTGCGCTGGATGAGCTGATT
GACACCTACGAGCACAAAGTCGGCCCCCGAAACGGCGCACAGGTTGTCGCCAGAGCGTGGAGC
GACCCGGAATACAAACGTCGACTGATGGAAAACGCCACTGCCGCTATTGCTGAACTGGGTTTC
TCCGGAATACAGGGCGAAGACATGCTGGTCGTGGAGAACACGCCGGACGTGCACAACGTCACC
GTTTGTACGCTGTGTTCCTGCTACCCCTGGCCGGTACTGGGTCTGCCGCCGGTGTGGTACAAA
TCAGCGCCCTATCGTTCGCGTATCGTCATCGACCCGCGCGGCGTTCTCGCCGAGTTCGGGTTA
CACATACCAGAAAACAAAGAGATTCGCGTCTGGGATAGCAGCGCCGAGCTGCGCTATCTGGTC
CTGCCTGAACGTCCGGCAGGCACGGAAGGCTGGAGCGAAGCGCAGTTGAGCGAACTCATCACG
CGCGATTCGATGATTGGCACCGGTGTGGTTACCGCACCATAA

Figure 18    Seq ID No. 18 (Klebsiella oxytoca, strain 38.1.2) α-subunit

MSHKHDHDHTQPPVDIELRVRALESLLQEKGLIDPAALDELIDTYEHKVGPRNGAQVVARAWS
DPEYKRRLMENATAAIAELGFSGIQGEDMLVVENTPDVHNVTVCTLCSCYPWPVLGLPPVWYK
SAPYRSRIVIDPRGVLAEFGLHIPENKEIRVWDSSAELRYLVLPERPAGTEGWSEAQLSELIT
RDSMIGTGVVTAP

Figure 19    Seq ID No. 19 (Klebsiella oxytoca , strain 38.1.2) β-subunit

ATGAACGGGATACACGATCTGGGGGGGATGCACGGCCTTGGCCCGATCCCTACCGAGGAAAAC
GAGCCCTATTTCCATCATGAGTGGGAACGCCGGGTATTTCCTCTGTTCGCCTCGTTGTTCGTC
GGCGGACACTTTAACGTCGATGAATTTCGCCACGCCATCGAACGTATGGCGCCGACCGAATAT
CTGCAGTCGAGCTACTACGAGCACTGGCTGCATGCATTCGAAACGCTGCTGCTGGCAAAGGGG
GTGATCACCGTTGAAGAACTGTGGGGTGGCGCGAAGCCTGCCCCCTGCAAGCCTGGCACACCT
GTGCTGACGCAGGAGATGGTGTCGATGGTGGTCAGCACCGGCGGGTCTGCTCGGGTCAGTCAC
GATGTTGCGCCCCGCTTCCGGGTGGGCGATTGGGTACGAACGAAAAATTTCAACCCGACCACC
CATACCCGCCTGCCACGCTACGCACGCGATAAAGTCGGTCGCATAGAGATCGCTCACGGTGTG
TTTATCACGCCAGATACTGCGGCGCACGGGCTGGGCGAACATCCCCAACATGTTTACAGCGTC
AGTTTCACCGCGCAGGCGCTATGGGGAGAGCCGCGCCCTGACAAAGTGTTCATCGATCTGTGG
GACGACTATCTGGAGGAAGCATAA

Figure 20    Seq ID No. 20 (Klebsiella oxytoca, strain 38.1.2) β-subunit

MNGIHDLGGMHGLGPIPTEENEPYFHHEWERRVFPLFASLFVGGHFNVDEFRHAIERMAPTEY
LQSSYYEHWLHAFETLLLAKGVITVEELWGGAKPAPCKPGTPVLTQEMVSMVVSTGGSARVSH
DVAPRFRVGDWVRTKNFNPTTHTRLPRYARDKVGRIEIAHGVFITPDTAAHGLGEHPQHVYSV
SFTAQALWGEPRPDKVFIDLWDDYLEEA

Figure 21   Seq ID No. 21 (Brevibacterium linens, strain, 32B.1) P16K

ATGACCGCCACCTCGGTCCGAGCCGATACCACAGAACTCGGCGATGCACGCCGCCGGGTG
GAGAAACTCGTCTGCAGCCTGCCCGGCGCACCGGGCGGTGACACTGCGTTCACCGCACCA
TGGGAGATACGCGCTTTCGCGATGGCAGTGGCCGCCTACGACGCACGCCAGTTCGAATGG
TCCGAATTCCAGCTCTCCTTGATCGAGTCGATCAAGTACTGGGAAGAAAACGAAGGTGAA
TCCGAACAGACATCGTGGTCGTACTACGAGCATTGGCTTAACGCGCTCGAAACCCGCCTG
TCCGAGAGCGGACTGCTCAGCGACGCCGACCTCGACGAGCGCACCACAACAGTGCTCGCC
ACCCCGCCCGATCGCGACCACCACAAAGCACACCTCGAACCAGTGAGCATCGATCCCGCC
CGCATTCCTTAG

Figure 22   Seq ID No. 21 (Brevibacterium linens, strain, 32B.1) P16K

MTATSVRADTTELGDARRRVEKLVCSLPGAPGGDTAFTAPWEIRAFAMAVAAYDARQFEW
SEFQLSLIESIKYWEENEGESEQTSWSYYEHWLNALETRLSESGLLSDADLDERTTTVLA
TPPDRDHHKAHLEPVSIDPARIP

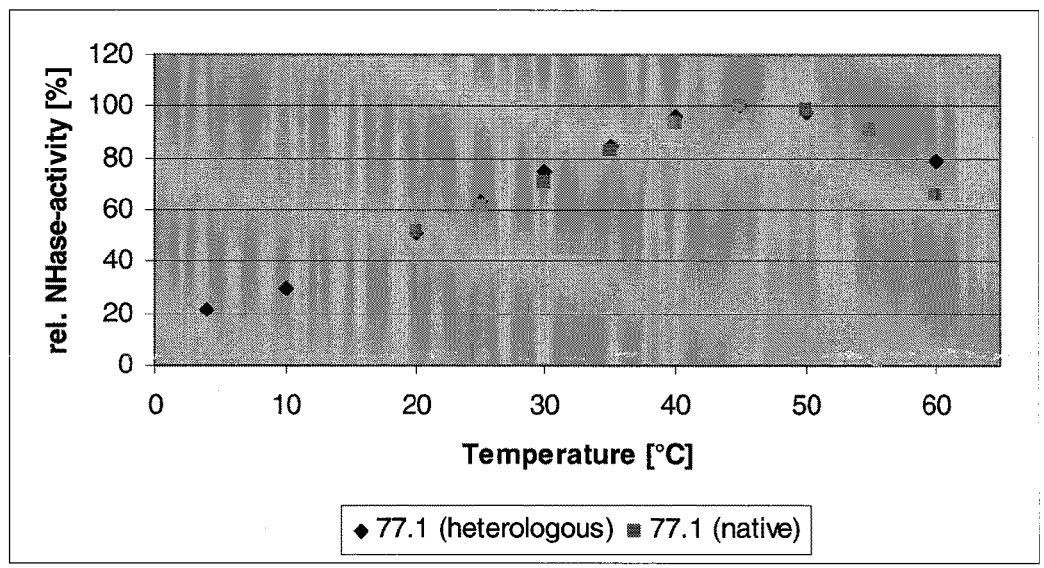

Figure 23

GROUP OF NOVEL ENANTIOSELECTIVE MICROBIAL NITRILE HYDRATASES WITH BROAD SUBSTRATE SPECIFICITY

This application is the National Phase of International Application PCT/EP2007/003114, filed Apr. 5, 2007 which designated the U.S. and that International Application was published under PCT Article 21(2) in English, and claims priority to European Application Serial No. 06 00 7383.0, filed Apr. 7, 2006.

The present invention provides a polynucleotide or a pair of polynucleotides encoding an enzyme having nitrile hydratase (NHase) [E.C. 4.2.1.84] activity. Furthermore, a vector and a host comprising the disclosed polynucleotide or pair of polynucleotides and methods for the production of the same are provided. Moreover, the invention relates to polypeptides or a fusion protein having NHase activity, an antibody specifically binding to the polypeptides or fusion protein, a primer or probe which specifically hybridizes under stringent conditions to the disclosed polynucleotide or either one of the pair of polynucleotides, a composition comprising the polynucleotide or pair of polynucleotides, the polypeptides or fusion protein, the antibody and/or one or more primers or probes of the invention and a method for the production of amides comprising the enantioselective conversion of nitriles.

A variety of documents is cited throughout this specification. The disclosure content of said documents including manufacturer's manuals is herewith incorporated by reference in its entirety.

NHases are typically composed of two different subunits (α and β) building heteromultimers, usually heterodimers or heterotetramers [1]. The subunits typically have molecular weights ranging from 22-28 kDa. In bacteria the structural genes of NHases are located usually in a cluster comprising also the genes encoding an amidase, regulatory proteins and in certain cases an NHase activator protein [2, 3, 4]. It seems that the physiological role of NHases in bacteria is the metabolism of plant derived aldoxims, since the ability to convert aldoxims to nitrites by aldoxim dehydratase and nitrile converting activity are tightly coupled [5].

NHases are metalloenzymes, containing a non-heme iron or a non-corrinoid cobalt atom at the catalytic site [6]. All the metal ion protein ligands are contained within the α-subunit [7]. Spectroscopic and three-dimensional structure analysis of NHases revealed that the metal atoms were found on five verticals of an octahedron. The ligands were found to be located in the conserved sequence motif "-V-C-(T/S)-L-C-S-C-"; the ligands being three cystein thiolate and two main chain nitrogen atoms. Two of the cysteins were found to be posttranslationally oxidized to cystein-sulfinic and cystein-sulfenic acids. The cobalt NHases have a threonine residue in the conserved active-site motif, whereas the ferric NHases have a serine.

The requirement of other proteins for the production of active NHases from different organisms has been reported [5, 8, 9, 10]. While small proteins (12-16 kDa) homologous to the N-terminus of NHase β-subunits (β-homologues) are associated with the cobalt-dependent enzymes, the corresponding proteins of the iron-dependent NHases have a molecular weight of 43-47 kDa [2]. These "activators" might be involved in the incorporation of the cofactor into the active site of NHases [11]. However, not for all NHases activator proteins have been described and in the case of the NHases from the thermophile *Bacillus* sp. BR449 [12] and *Bacillus* sp. RAPc8 [2] homologous genes were identified downstream of the NHase structural genes which are not necessary for the functional expression.

Biotransformations using microbial nitrile and amide-converting enzymes have developed considerably in recent years [13]. The large scale NHase-catalysed synthetic processes for the production of acrylamide, nicotinamide and 5-cyanovaleramide are outstanding examples of the use of enzymes in an industrial environment [14].

Products intended for use in biological systems must often be synthesized in a particular enantiomeric form due to preferences that correlate with the "handedness" (i.e., optical rotation) of the molecule. For example, only the (S)-form of the widely prescribed anti-inflammatory Naproxen (2-(6-methoxy-2-naphthyl)propionic acid) is clinically effective. The (R)-form is toxic [15]. Therefore, the drug must be supplied such that the (S)-enantiomer, and not the (R)-enantiomer, is highly enriched in the final product. A similar situation exists for many other pharmaceutical and agricultural chemicals. However, the synthesis chemist is often faced with a difficult problem because most chemical catalysts do not discriminate by optical form. In fact, it is very difficult to synthesize a single enantiomer. Moreover, because enantiomers, by definition, have identical physical properties and differ only in the direction that they rotate plane polarized light, separation of individual enantiomers from a mixture of (S)- and (R)-enantiomers is difficult [16].

The stereopreference of an enzyme is described by the enantiomeric excess (ee) which is given by the formula $$ee_p = \frac{[P1] - [P2]}{[P1] + [P2]}$$

where P1 and P2 are the concentrations of the two stereoisomers in the reaction product and P1 is present in a higher concentration than P2. However, this term is not sufficient to describe the enantioselectivity of an enzyme since the term "ee" depends on the degree of conversion of the substrate. Initially the preferred substrate will be converted faster to the product P1 than the non-preferred substrate to product P2 so that the concentration of the preferred substrate will decrease during the reaction. This in turn will lead to an increased conversion of the non-preferred substrate and to a decrease in $ee_P$ with increasing conversion.

Thus the enantioselectivity of an enzyme is better described by the term "E" given by the formula $$E = \frac{\ln[1 - \xi(1 + ee_{product})]}{\ln[1 - \xi(1 - ee_{product})]}$$

where the conversion $\xi$ is given by $$\xi = \frac{1}{1 + \dfrac{C_{substrat}}{C_{product}}}$$

$C_{substrate}$ and $C_{product}$ denote the concentrations of the substrates and products, respectively. [17, 18]

The apparent enantiomeric ratio ($E_{app}$) is used in the case of asymmetric catalysis. $E_{app}$ is calculated from $$E_{app} = \frac{1+ee_p}{1-ee_p}$$

as described by Straathof and Jongejan, 1997 [41].

NHases with an enantiopreference for certain cyanohydrine substrates were described for a few genera of bacteria, namely *Pseudomonas, Agrobacterium, Rhodococcus, Moraxella* and *Serratia* (Tables 1+2). However, the enantioselectivity given as E-value of NHases was determined only in very few cases (Table 2).

Although there are numerous publications describing possible biotransformations using NHases as summarized by Cowan et al. [1], the limited availability of novel and well-characterised NHases especially with respect to enantioselectivity and substrate specificity [6] restricts their application in industrial processes [13].

Thus, the technical problem underlying the present invention was to provide means and methods for an improvement of the spectrum of enzymes capable of the enantioselective catalysis of nitriles to the corresponding amides. The provision of such enzymes is expected to increase the efficiency of the conversion and further reduce the costs for the industrial applications of the produced amides. The solution to this technical problem is achieved by the embodiments characterized in the claims.

Accordingly, the present invention relates in a first embodiment to a polynucleotide or a pair of polynucleotides encoding an enzyme having nitrile hydratase (NHase) [E.C. 4.2.1.84] activity, wherein the coding sequence is selected from the group consisting of:

(a) a polynucleotide or a pair of polynucleotides having or comprising a nucleotide sequence encoding an α-subunit of the NHase having the amino acid sequence as shown in one of SEQ ID NOs: 2, 6, 10, 14 and 18, and a β-subunit of the NHase having the amino acid sequence as shown in one of SEQ ID NOs: 4, 8, 12, 16 and 20;

(b) a polynucleotide or a pair of polynucleotides having or comprising a nucleotide sequence as shown in one of SEQ ID NOs: 1, 5, 9, 13 and 17 and encoding an α-subunit of the NHase, and a nucleotide sequence as shown in one of SEQ ID NOs: 3, 7, 11, 15 and 19 and encoding a β-subunit of the NHase;

(c) a polynucleotide or a pair of polynucleotides having or comprising a nucleotide sequence encoding a fragment or derivative of the NHase encoded by the polynucleotide or pair of polynucleotides of any one of (a) or (b), wherein in said derivative one or more amino acid residues are conservatively substituted compared to said polypeptide;

(d) a polynucleotide or a pair of polynucleotides comprising a nucleotide sequence which is at least 75% identical to a polynucleotide encoding the α-subunit of the NHase as shown in one of SEQ ID NOs: 9 or 13 or the β-subunit of the NHase as shown in one of SEQ ID NOs: 11 or 15, at least 85% identical to a polynucleotide encoding the β-subunit of the NHase as shown in one of SEQ ID NOs: 3, 7 or 19, or at least 90% identical to a polynucleotide encoding the α-subunit of the NHase as shown in one of SEQ ID NOs: 1, 5 or 17;

(e) a polynucleotide or a pair of polynucleotides having or comprising a nucleotide sequence the complementary strand of which hybridizes to a polynucleotide or pair of polynucleotides as defined in any one of (a) to (d); and (f) a polynucleotide or a pair of polynucleotides having or comprising a nucleotide sequence being degenerate to the nucleotide sequence of the polynucleotide or pair of polynucleotides of (d) or (e);

or the complementary strand or pair of complementary strands of such a polynucleotide or pair of polynucleotides of (a) to (f) or fragments thereof useful as specific probes or primers.

In accordance with the present invention, the fragment, derivative etc. encoded by the polynucleotide or pair of polynucleotides of any items (c) to (f) retains or essentially retains NHases enzymatic activity.

An enzyme having nitrile hydratase (NHase) [E.C. 4.2.1.84 according to the IUBMB Enzyme Nomenclature] activity is capable to convert nitrile to the corresponding amide. Assays for the determination of the characteristic activity profile of a given enzyme are known in the art. A characteristic activity profile for a NHase can be determined as described in Bauer et al, 1998 [22]. Briefly, cells showing NHase activity are washed and resuspended e.g. in sodium/potassium phosphate buffer (50 mM pH 7.4). Cell suspensions are incubated with the substrates in a final concentration of 0.5-1 mM under defined conditions with respect to temperature and shaking. Cells are removed by centrifugation from aliquots taken in defined intervals.

The supernatants are analyzed by HPLC. These assays can be employed by the skilled artesian without further ado in the determination whether e.g. a fragment or derivative or homolog etc. encoded by the polynucleotide or pair of polynucleotides in any of items (c) to (f), above, will retain or essentially retain NHase activity.

In accordance with the present invention, activity is essentially retained, if at least 20% of the enzymatic activity of the corresponding "wild type" enzyme recited in items (a) or (b), supra, is obtained, preferably applying one of the test formats described herein above in the context of the determination of the enzyme activity of NHases of the state of the art. Preferably, at least 50, such as at least 60%, at least 75% or at least 80% of the activity are retained. More preferred is that at least 90% such as at least 95%, even more preferred at least 98% such as at least 99% of the enzymatic activity are retained. Most preferred is that the enzymatic activity, i.e. the capacity to convert nitrites to the corresponding amides, is fully, i.e. to 100% retained. Also in accordance with the invention is an enzyme having increased NHase activity compared to the corresponding wild type enzyme, i.e. more than 100% enzyme activity of the reference wild type enzyme.

A reduced or enhanced enzymatic activity as compared to the corresponding "wild type" enzyme may be a consequence of e.g. the substitution of one of the three cysteines in the consensus motif "C—S/T-L-C-S-C" in the α-subunits of NHases [23], of the substitution of the threonine (T) in the consensus motif "C-T-L-C-S-C" of cobalt-dependent NHases [24], of the substitution of a conserved tyrosine (Y) in the β-subunits of NHases [24], of the substitution of two conserved arginines (R) in the β-subunits of NHases [25, 26], of the replacement of a conserved tyrosine (Y) residue which follows the consensus motif "C-T-L-C-S-C" in cobalt-dependent NHases [24], of the expression of the genes encoding the subunits of the NHase in host cells in a medium lacking the necessary metal ion [cobalt or iron] [24] or supplying only the metal ion not found in the wild type NHase [27], of the expression of the genes encoding the subunits of the NHase in the absence of the corresponding activator protein [5,8,9,10], or of any other pertubation of the ligand set necessary to coordinate the metal ion essential for catalysis.

As outlined herein above, a NHase is typically composed of an α- and a β-subunit. In line with the invention the α- and the β-subunit of a NHase may be derived from two different organisms of the same strain, two different strains of the same species, two different species of the same genus or from two different genera. Alternatively, the subunits are derived from the organisms of the same genus, more preferred from the same species, or even more preferred form the same strain. Preferably, the genera from which the subunits are derived from are selected from the group of genera consisting of *Raoultella, Pantoea, Brevibacterium* and *Klebsiella*. More preferably, the α- and the β-subunits of a NHase are derived from *Raoultella terrigena*, strain 77.1 or strain 37.1, *Pantoea* sp., strain 17.3.1, *Brevibacterium* linens, strain 32B.1 or *Klebsiella oxytoca*, strain 38.1.2. The isolation of the corresponding strains has been reported by Hensel et al. 2002 [28].

According to the present invention, it is generally preferred that, in the case of a pair of polynucleotides, one of the polynucleotides encodes the α-subunit of the NHases whereas the second polynucleotide of the pair of polynucleotides encodes the β-subunit.

In accordance with the present invention the term "polynucleotide" defines a nucleic acid molecule consisting of more than 30 nucleotides. The group of molecules subsumed under polynucleotides also comprise complete genes. Also included by said definition are vectors such as cloning and expression vectors.

The term "oligonucleotides" describes in the context of the invention nucleic acid molecules consisting of at least ten and up to 30 nucleotides.

Nucleic acid molecules, in accordance with the present invention, include DNA, such as cDNA or genomic DNA, RNA (e.g. mRNA), also in synthetic or semisynthetic form, further synthetic or semisynthetic derivatives of DNA or RNA (e.g. PNA or phosphorothioates) and mixed polymers, both sense and antisense strands. They may contain additional non-natural or derivatized nucleotide bases, as will be readily appreciated by those skilled in the art. In a preferred embodiment of polynucleotide or pair of polynucleotide the nucleic acid molecule(s) is/are DNA.

For the purposes of the present invention, a peptide nucleic acid (PNA) is a polyamide type of DNA analog and the monomeric units for the derivatives of adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In those embodiments where the polynucleotide or pair of polynucleotides comprises (rather than have) the recited sequence, additional nucleotides extend over the specific sequence either on the 5' end or the 3' end or both. Those additional polynucleotides may be of heterologous or homologous nature and may comprise stretches of about 50 to 500 nucleotides although higher or lower values are not excluded. In the case of homologous sequences, those embodiments do not include complete genomes and are generally confined to about 1000 additional nucleotides at the 5' and/or the 3' end. Additional heterologous sequences may include heterologous promoters which are operatively linked to the coding sequences of the invention.

The term "polypeptide" as used herein describes a group of molecules which consist of more than 30 amino acids. In accordance with the invention, the group of polypeptides comprises "proteins" as long as the proteins consist of a single polypeptide. Also in line with the definition the term "polypeptide" describes fragments of proteins as long as these fragments consist of more than 30 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example of a heteromultimer is a NHase according to the invention, which exists as heterodimer, a heterotetramer or even higher numbers of pairs of subunits. Homodimers, trimers etc. of fusion proteins, wherein each single fusion protein comprises at least one α-subunit and one β-subunit, giving rise or corresponding to enzymes such as the NHases of the present invention also fall under the definition of the term "protein". Furthermore, peptidomimetics of such proteins/polypeptides wherein amino acid(s) and/or peptide bond(s) have been replaced by functional analogs are also encompassed by the invention. Such functional analogues include all known amino acids other than the 20 gene-encoded amino acids, such as selenocysteine. The terms "polypeptide" and "protein" also refer to naturally modified polypeptides/proteins wherein the modification is effected e.g. by glycosylation, acetylation, phosphorylation and the like. Such modifications are well known in the art.

The term "enzyme" defines in the context of the invention a polypeptide, polypeptides and/or protein(s), all comprising at least one α-subunit and one β-subunit according to the invention (as well as higher mulitmeric structures thereof) and having a specific NHase enzymatic activity.

Methods and algorithms for exchanging one or more nucleotides in the polynucleotide or pair of polynucleotides in item (c), supra, wherein the exchange gives rise to a conservative substitution of one or more amino acid residues in a given polypeptide are known in the art; see e.g. Barettino et al. 1994 [29], Urban et al. 1997 [30] or Seyfang & Jin 2004 [31].

In accordance with the present invention, the term "percent identity" describes the number of matches ("hits") of identical nucleotides/amino acids of two or more aligned nucleic acid or amino acid sequences as compared to the number of nucleotides making up the overall length of the nucleic acid or amino acid sequences (or the overall compared part thereof). In other terms, using an alignment, for two or more sequences or subsequences the percentage of amino acid residues or nucleotides that are the same (e.g., 60% or 65% identity) may be determined, when the (sub)sequences are compared and aligned for maximum correspondence over a window of comparison, or over a designated region as measured using a sequence comparison algorithm as known in the art, or when manually alignment and visually inspected. This definition also applies to the complement of a test sequence. Preferred polynucleotides/polypeptides in accordance with the invention are those where the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTA [19], as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands. Ali those programs may be used for the purposes of the present invention. All of the above programs can be used in accordance with the invention.

The values for the % identity are identified herein always with regard to a single subunit. Accordingly, for a single polynucleotide, which encodes an α- and a β-subunit of a NHase according to the invention, the % identity value to a second polynucleotide is calculated separately in alignments of the subsequences for the α-subunit and for the β-subunit.

The term "hybridizes/hybridizing" as used herein refers to a pairing of a polynucleotide to a (partially) complementary strand of this polynucleotide which thereby form a hybrid. Said complementary strand polynucleotides are, e.g. the polynucleotides described in item (e), supra, or parts of polynucleotides comprising at least 10, preferably at least 15 such as at least 25 consecutive nucleotides thereof, if used as primers or probes. Said complementary polynucleotides may be useful as probes in Northern or Southern blot analysis of RNA or DNA preparations, PCRs and the like or primer extension protocols respectively. In this connection, the term "fragments thereof useful as specific probes or primers" refers to nucleic acid molecules the sequence of which is uniquely fitting to (hybridizing to/complementary to preferably 100%) the sequences of the nucleic acid molecules described in accordance with the present invention, but not to prior art sequences. The skilled person can identify such fragments by simple sequence alignments. For example, if there is a 100% stretch of identity with a prior art sequence, the addition of a further nucleotide to that sequence of identity will yield a novel sequence which is encompassed by the present invention, since it is to 100% complementary to the polynucleotide of the invention but not to the prior art sequence. Hybridizing polynucleotides of the present invention to be used as a probe in Southern or Northern blot preferably comprises at least 100, more preferably at least 200, and most preferably at least 500 nucleotides in length. As regards those polynucleotides or pairs of polynucleotides that hybridize to the complementary strand of the specifically disclosed polynucleotide sequences and retain or essentially retain NHase activity must encode at least the active center of the enzyme.

It is well known in the art how to perform hybridization experiments with nucleic acid molecules. Correspondingly, the person skilled in the art knows what hybridization conditions s/he has to use to allow for a successful hybridization in accordance with item (e), above. The establishment of suitable hybridization conditions is referred to in standard text books such as Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). In one preferred embodiment, the hybridization is effected is under stringent conditions.

"Stringent hybridization conditions" refers to conditions which comprise, e.g. an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Said conditions for hybridization are also known by a person skilled in the art as "highly stringent conditions for hybridization". Also contemplated are nucleic acid molecules that hybridize to the polynucleotides of the invention at lower stringency hybridization conditions ("low stringency conditions for hybridization"). Changes in the stringency of hybridization and signal detection are primarily accomplished through the manipulation of formamide concentration (lower percentages of formamide result in lowered stringency), salt conditions, or temperature. For example, lower stringency conditions include an overnight incubation at 37° C. in a solution comprising 6×SSPE (20×SSPE=3M NaCl; 0.2M NaH$_2$PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve an even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Such modifications can generally be effected by the skilled person without further ado. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The embodiment recited herein above preferably refers to highly stringent conditions and alternatively to conditions of lower stringency.

Further to the above, the term "a polynucleotide or a pair of polynucleotides having a nucleotide sequence the complementary strand of which hybridizes to a polynucleotide or pair of polynucleotides as defined in any one of (a) to (d)" as recited in item (e) preferably refers to sequences which display a sequence identity of at least 70%, preferably of at least 80%, more preferred of at least 90%, even more preferred of at least 95% and most preferred of at least 97% with a nucleotide sequence as described above in items (a) or (b) encoding an enzyme having NHase activity of the invention.

As stated herein above, preferred in accordance with the present invention are polynucleotides which are capable of hybridizing to the polynucleotides of the invention or parts thereof, under (highly) stringent hybridization conditions, i.e.

which do not cross hybridize to polynucleotides unrelated in nucleotide sequence. In accordance with item (e), above, polynucleotides related but not identical in sequence with the polynucleotides of items (a) and (b) are also encompassed by the invention. In addition, the invention comprises according to item (e) fragments of the polynucleotides of (a) and (b). For all embodiments falling under item (e), it is essential that they retain or essentially retain the enzymatic function of the NHase of the invention. In addition, it is essential in accordance with this embodiment, that the complementary strand of the polynucleotide of item (e) hybridizes to the polynucleotide of (a) or (b), preferably under stringent conditions. (The latter requirement is self-evident for fragments of polynucleotides of items (a) or (b) that retain enzymatic activity.) Also encompassed by the polynucleotides of item (e) are allelic variants of polynucleotides of items (a) and (b).

Polynucleotides are (partially) "complementary" if they naturally bind to each other under permissive salt and temperature conditions by base-pairing. For example, the sequence "A-G-T" binds to the complementary sequence "T-C-A". Complementarity between two single-stranded molecules may be "partial", in which only a portion of the nucleotides base pair, or it may be complete when all nucleotides over a given length base-pair. The degree of complementary between nucleic acid strands has significant effects on the efficiency and strength of hybridization between nucleic acid strands. This is of particular importance in nucleic acid amplification reactions, which depend upon binding between nucleic acids strands.

Moreover, the present invention also relates to nucleic acid molecules the sequence of which is degenerate in comparison with the sequence of an above-described polynucleotide of item (d) or (e). When used in accordance with the present invention the term "being degenerate as a result of the genetic code" means that due to the redundancy of the genetic code different nucleotide sequences code for the same amino acid.

It has been surprisingly found that the above described polynucleotides or pairs of polynucleotides encode novel NHases with a characteristic substrate specificity, enantioselectivity, reaction velocity, structure and/or reaction mechanism which is/are different compared to the ones of enzymes known in the art.

The enzymes of strains *Raoultella terrigena*, strain 77.1 (Seq ID No. 2 and 4), *Raoultella terrigena*, strain 37.1 (Seq ID No. 6 and 8) and *Klebsiella oxytoca*, strain 38.1.2 (Seq ID No. 18 and 20) are characterized by the presence of the following motives in the primary structure of the α-subunit and/or β-subunit which are not present in anyone of the enzymes in the state of the art:

α-Subunits:

"F-G-L-H-I-P" where other NHases are characterized by a sequence given by the motif [F, V, M, L]-[G, D, N, K]-[L, T, H, V, Y, F]-[S, H, E, D, T, A, P, N, R, K, V, M, I]-[L, F, I, P]

"S-E-L-I" where other NHases are characterized by a sequence given by the motif [S, A, M, E, V, T, I, Q, R]-[E, A, S, D, P, T, K, Q, G, L]-[I, L, R]-[I, V, L]

"V-V-T-A-P" where other NHases are characterized by a sequence given by the motif [L, V, P, N, K, R, G, F, I, D, E]-[P, T, A, V, D, E, I, L, C]-[K, Q, R, T, G, A, V, L, E, S, F, I, H]-[P, D, L, Q, A, R, T, K, S, E, N, Y, G, I, V]-[G, D, P, T, A, E, V, L, Q, H, V, S, P, I]

β-Subunits:

"P-I-P-T" where other NHases are characterized by a sequence given by the motif [K, Q, P, R, A, L, G, V]-[V, I, L, N, P]-[P, D, R, E, K, I, M, Y, A, L, Q, N, V, K, T]-[H, Y, I, A, K, R, P, N, L, Q, T, D, S, V]

"Q-S" where other NHases are characterized by a sequence given by the motif [M, G, A, T, K, E, Q, R, S, N, D, L]-[T, A, L, S, G, M, V, K, F, Y, N]

"L-A" where other NHases are characterized by a sequence given by the motif [V, T, I, L, A, S, E, A, K, R, Q, N]-[E, D, L, R, S, A, H, N, Q]

"T-V" where other NHases are characterized by a sequence given by the motif [T, A, N, D, S, G, E, D, R]-[Q, H, R, E, S, P, A, I, M]

"A-K-P" where other NHases are characterized by a sequence given by the motif [A, L, I, M, T, S, R, E, H, K, V, G, D]-[G, Q, A, R, E, K, T, P, M, S, D, A, E, H]-[G, S, E, V, A, Q, P, L, I, R, M, T, D, F, Y]

"C-K-P-G-T-P" where other NHases are characterized by a sequence given by the motif [I, L, G, C, A, T, R, S, K, V, P, H, E]-[P, Q, K, A, V, E, T, S, M, N, D, G, R, I, H]-[R, T, Q, P, K, I, G, V, L, A, E]-[R, W, T, A, I, G, S, K, P, N, V, Q, D, E]-[E, D, T, M, R, A, H, K, E, S, Q, F, N]-[D, N, R, P, A, G, K, L, T, Q]

"S-M-V-V" where other NHases are characterized by a sequence given by the motif [R, N, M, S, E, A, D, Q, T, P, G, V, I]-[P, C, V, K, A, G, M, D, S, R, Q, E, L]-[S, A, P, N, V, L, I, Y, T, M, R]-[E, H, R, A, V, L, D, M, Y, W, P, T]

"G-G-S" where other NHases are characterized by a sequence given by the motif [G, P, K, A, L, E, L, I, F]-[R, T, V, I, P, L, S, A, K, F, D, H]-[P, A, S, T, G, E, D, K, Y]

"V-A-P" where other NHases are characterized by a sequence given by the motif [E, D, G, A, P, V, S, K, I, T, Q, R]-[T, R, S, A, Q, G, F, P, E, H, I]-[T, I, A, P, E, H, S, Q, F, G]

"R-V-G" where other NHases are characterized by a sequence given by the motif [E, Q, A, D, R, K, T, P, V, S, N, G]-[V, I, P, A, T, F, R, L, E]-[G, S]

"E-I-A" where other NHases are characterized by a sequence given by the motif [H, S, T, E, D, V, W, L, Q, A, C, I]-[R, E, L, S, I, T, A, C, K, Q]-[T, S, V, C, I, L, H, D, N, K, Q, F, Y, M]

"E-P-R-P" where other NHases are characterized by a sequence given by the motif [S, D, A, G, Q, T, E, P, H, V, K]-[D, A, S, V, Y, E, P, T, G, R, Q, N]-[T, A, R, Y, V, S, D, G, C, P, E, K]-[D, G, H, K, E, S, P, R, T, A, N]

"V-F-I" where other NHases are characterized by a sequence given by the motif [V, A, L, I, T, N]-[V, L, H, E, N, Y, M, R, Y, S, C, T, I]-[V, A, I, M, L, Y, F]

The sequence comparisons were based on a ClustalX—alignment of complete and non-redundant protein sequences of α- and β-subunits available at the NCBI. The protein entries in NCBI's Entrez search and retrieval system have been compiled from a variety of sources, including SwissProt, PIR, PRF, PDB, and translations from annotated coding regions in GenBank and RefSeq. These databases were searched by the key word: "nitrile hydratase". From these sequences a Hidden Markov Model (HMM) was build and used to search the environmental database. These entries were then included in the alignment.

Furthermore, the enzymes of strains *Raoultella terrigena*, strain 77.1 (Seq ID No. 2 and 4), *Raoultella terrigena*, strain 37.1 (Seq ID No. 6 and 8) and *Klebsiella oxytoca*, strain 38.1.2 (Seq ID No. 18 and 20) are characterized by higher enantioselectivities towards rac-mandelonitrile and rac-2-phenylpropionitrile than reported for any other nitrile hydratase. The recombinant enzyme comprising the polypeptides according to Seq ID Nos. 2 and 4 (*Raoultella terrigena* 77.1) showed an enantiopreference for the (S)-isomer of (R/S)-mandelonitrile with an $E_{app}$-value of 20. For the enzymes comprising the polypeptides according to Seq ID Nos. 6 and 8 (*Raoultella terrigena* 37.1) an $E_{app}$-value of 18 was observed in the kinetic resolution of this substrate with a preference for the (S)-enantiomer. The recombinant enzyme comprising the polypeptides according to Seq ID Nos. 18 and 20 (*Klebsiella oxytoca* 38.1.2) showed an enantiopreference for the (S)-isomer of (R/S)-mandelonitrile with an $E_{app}$-value of 19. For the enzymes comprising the polypeptides according to Seq ID Nos. 10 and 12 (*Pantoea* sp. 17.3.1) and Seq ID Nos. 14 and 16 (Brevibacterium lines 32B.1) $E_{app}$-value of 4 were observed in the kinetic resolution of this substrate with a preference for the (S)-enantiomer. The bacterial strain *Rhodococcus* sp. HT40-6 was reported to convert racemic mandelonitrile enantioselectively also with a preference for the (S)-enantiomer, but no E-values were given for this conversion (EP 0711836). Furthermore, the enzymes comprising the polypeptides according to Seq ID Nos. 2 and 4 (*Raoultella terrigena* 77.1), according to Seq ID Nos. 6 and 8 (*Raoultella terrigena* 37.1), according to Seq ID Nos. 10 and 12 (*Pantoea* sp. 17.3.1), according to Seq ID Nos. 14 and 16 (Brevibacterium lines 32B.1) and according to Seq ID Nos. 18 and 20 (*Klebsiella oxytoca* 38.1.2) were found to be enantioselective in the kinetic resolution of rac-2-phenylpropionitrile with a preference for the (S)-enantiomer and with E-values of 47, 47, 2, 8 and 35 respectively. The bacterial strain *Agrobacterium tumefaciens* strain d3 was reported to convert rac-2-phenylpropionitrile enantioselectively, also with a preference for the (S)-enantiomer. For the amide formed from this compound, an ee value above 90% was observed until about 30% of the respective substrate was converted but no E value was given for this conversion (Bauer et al., 1998 [22]). An enantioselectivity of E=253 was calculated from these data by Martinkova & Kren (2002) in a review article. However, the original literature from Bauer et al., 1998 [22] and Bauer, 1997 Dissertation University of Stuttgart) which was cited by Martinkova & Kren did not provide these data. Therefore, there is no experimental evidence for such a high enantioselectvity towards 2-phenylpropionitrile.

The enzyme comprising polypeptides according to Nos. 2 and 4 (*Raoultella terrigena* 77.1) and according to Seq ID Nos. 18 and 20 (*Klebsiella oxytoca* 38.1.2) surprisingly showed a broad substrate specificity converting a series of aromatic as well as aliphatic nitriles as given in table 16.

The low-molecular mass nitrile hydratase from *Rhodococcus rhodochrous* J1 was reported also to convert aromatic and aliphatic nitriles (Wieser et al, 1998 [32]). A preference for one enantiomer in the conversion of racemic nitriles was not reported.

As described herein above, the presence of proteins for the production of active NHases is required in some organisms. Accordingly, when these specific NHases are recombinantly expressed in a host, an active enzyme is produced only when the required activator protein(s) is/are present in the host. In contrast, the recombinant expression of polynucleotides of the invention encoding polypeptides with NHase activity does not require the presence of such activator proteins in a host, although their presence may increase the activity. This is even true for the NHase enzyme consisting of the α- and β-subunits encoded by SEQ ID NOs: 13 and 15 which are isolated from Brevibacterium linens, strain 32B.1, for which a gene for an activator, designated P16K, was identified. The nucleic acid sequence of the P16K gene isolated from Brevibacterium linens, strain 32B.1 is depicted in FIG. 21 (SEQ ID NO: 21). The amino acid sequence of the encoded protein is depicted in FIG. 22 (SEQ ID NO: 22).

The similarity of the polynucleotides according to Seq ID NOs: 1, 3, 5, 7, 9, 11, 13, 15, 17 and 19 to other NHases encoding polynucleotides from the state of the art is given in Tables 3-12. The analysis was performed using the Fasta algorithm [19] using the following database: EMBL [20], GenBank [21]. Determining sequence homologies/identities with this method/those means is particularly preferred in accordance with the present invention.

In a preferred embodiment of the polynucleotide or a pair of polynucleotides of the invention said polynucleotide or a pair of polynucleotides is selected from:
(a) a polynucleotide or a pair of polynucleotides having or comprising a nucleotide sequence encoding pairs of α- and β-subunits of the NHase, wherein the pairs of subunits have the amino acid sequences: (i) SEQ ID NOs: 2 and 4, (ii) SEQ ID NOs: 6 and 8, (iii) SEQ ID NOs: 10 and 12, (iv) SEQ ID NOs: 14 and 16 or (v) SEQ ID NOs: 18 and 20;
(b) a polynucleotide or a pair of polynucleotides polynucleotide having or comprising a nucleotide sequence encoding pairs of α- and β-subunits of the NHase, wherein the pairs of nucleotide sequences are as shown in: (i) SEQ ID NOs: 1 and 3, (ii) SEQ ID NOs: 5 and 7, (iii) SEQ ID NOs: 9 and 11, (iv) SEQ ID NOs: 13 and 15, or (v) SEQ ID NOs: 17 and 19;
(c) a polynucleotide or a pair of polynucleotides having or comprising a nucleotide sequence encoding a fragment or derivative of the NHase encoded by a polynucleotide or pair of polynucleotides of any one of (a) or (b), wherein in said derivative one or more amino acid residues are conservatively substituted compared to said polypeptide;
(d) a polynucleotide or a pair of polynucleotides comprising a nucleotide sequence which is at least 75% identical to a polynucleotide encoding the α-subunit of the NHase as shown in one of SEQ ID NOs: 9 or 13 or the β-subunit of the NHase as shown in one of SEQ ID NOs: 11 or 15, at least 85% identical to a polynucleotide encoding the β-subunit of the NHase as shown in one of SEQ ID NOs: 3, 7 or 19, or at least 90% identical to a polynucleotide encoding the α-subunit of the NHase as shown in one of SEQ ID NOs: 1, 5 or 17 and wherein the polynucleotide or pair of polynucleotides have a nucleotide sequence encoding a pair of an α- and a β-subunit having the required identity with the pairs of nucleotide sequences of. (i) SEQ ID NOs: 1 and 3, (ii) SEQ ID NOs: 5 and 7, (iii) SEQ ID NOs: 9 and 11, (iv) SEQ ID NOs: 13 and 15, or (v) SEQ ID NOs: 17 and 19;
(e) a polynucleotide or a pair of polynucleotides having or comprising a nucleotide sequence the complementary strand of which hybridizes to a polynucleotide or pair of polynucleotides as defined in any one of (a) to (d); and
(f) a polynucleotide or a pair of polynucleotides having or comprising a nucleotide sequence being degenerate to the nucleotide sequence of the polynucleotide or pair of polynucleotides of (d) or (e);
or the complementary strand or a pair of complementary strands of such a polynucleotide or pair of polynucleotides of (a) to (f) or fragments thereof useful as specific probes or primers.

According to this preferred embodiment the polynucleotide or pair of polynucleotides has/have (a) sequence(s) encoding the α- and the β-subunit or the complementary strand of such a polynucleotide are derived from the same species.

The enzymes consisting of subunits having a sequence of the pairs of Seq. ID NOs: 2 and 4, 6 and 8, 10 and 12, 14 and 16 as well as 18 and 20 were found to convert rac-mandelonitrile enantioselectively with $E_{app}$-values as given in Table 13.

In an alternative embodiment the present invention relates to a polynucleotide or a pair of polynucleotides encoding an enzyme having nitrile hydratase (NHase) [E.C. 4.2.1.84] activity, wherein the coding sequence is selected from the group consisting of:

(a) a polynucleotide or a pair of polynucleotides having or comprising a nucleotide sequence encoding an α-subunit and a β-subunit of the NHase, wherein
  (i) the α-subunit has the amino acid sequence as shown in one of SEQ ID NOs: 2, 6, 10, 14 or 18; or
  (ii) the β-subunit of the NHase has the amino acid sequence as shown in one of SEQ ID NOs: 4, 8, 12, 16 or 20;
(b) a polynucleotide or a pair of polynucleotides having or comprising a nucleotide sequence encoding an α-subunit and a β-subunit of the NHase, wherein
  (i) the α-subunit has a nucleotide sequence as shown in one of SEQ ID NOs: 1, 5, 9, 13 or 17 and encoding an α-subunit of the NHase; or
  (ii) the β-subunit has a nucleotide sequence as shown in one of SEQ ID NOs: 3, 7, 11, 15 or 19 and encoding a β-subunit of the NHase;
(c) a polynucleotide or a pair of polynucleotides having or comprising a nucleotide sequence encoding a fragment or derivative of the NHase encoded by the polynucleotide or pair of polynucleotides of any one of (a) or (b), wherein in said derivative one or more amino acid residues are conservatively substituted compared to said polypeptide;
(d) a polynucleotide or a pair of polynucleotides comprising a nucleotide sequence encoding an α-subunit and a β-subunit of the NHase, wherein
  (i) the nucleotide sequence encoding the α-subunit of the NHase is at least 75% identical to a nucleotide sequence as shown in one of SEQ ID NOs: 9 or 13 or at least 90% identical to a nucleotide sequence as shown in one of SEQ ID NOs: 1, 5 or 17; or
  (ii) the nucleotide sequence encoding the β-subunit of the NHase is at least 75% identical to a nucleotide sequence as shown in one of SEQ ID NOs: 11 or 15 or at least 85% identical to a nucleotide sequence as shown in one of SEQ ID NOs: 3, 7 or 19;
(e) a polynucleotide or a pair of polynucleotides having or comprising a nucleotide sequence the complementary strand of which hybridizes to
  (i) the nucleotide sequence which encodes the α-subunit of the NHase which has the amino acid sequence as shown in one of SEQ ID NOs: 2, 6, 10, 14 or 18, or is a nucleotide sequence as shown in one of SEQ ID NOs: 1, 5, 9, 13 or 17 or encodes the α-subunit of the NHase which is at least 75% identical to a nucleotide sequence as shown in one of SEQ ID NOs: 9 or 13 or at least 90% identical to a nucleotide sequence as shown in one of SEQ ID NOs: 1, 5 or 17; or
  (ii) the nucleotide sequence which encodes the β-subunit of the NHase which has the amino acid sequence as shown in one of SEQ ID NOs: 4, 8, 12, 16 or 20, or is a nucleotide sequence as shown in one of SEQ ID NOs: 3, 7, 11, or 19 or encodes the β-subunit of the NHase which is at least 75% identical to a nucleotide sequence as shown in one of SEQ ID NOs: 11 or 15 or at least 85% identical to a nucleotide sequence as shown in one of SEQ ID NOs: 3, 7 or 19; and
(f) a polynucleotide or a pair of polynucleotides having or comprising a nucleotide sequence being degenerate to the nucleotide sequence of the polynucleotide or pair of polynucleotides of (d) or (e);
or the complementary strand or pair of complementary strands of such a polynucleotide or pair of polynucleotides of (a) to (f) or fragments thereof useful as specific probes or primers.

According to this alternative embodiment the polynucleotide or pair of polynucleotides of the invention encodes an enzyme having NHase activity which comprises at least one α-subunit and one β-subunit. A first subunit, which is an α- or a β-subunit corresponds to or is derivable from one of the polynucleotides as shown in SEQ ID NOs: 1, 5, 9, 13 or 17 or SEQ ID NOs: 3, 7, 11, 15 or 19. The second subunit, which completes the pair of the α- and the β-subunit, may be a subunit from a NHase of the state of the art which forms with the first subunit the enzyme having NHase activity.

A combination of an α- and a β-subunit from two different organisms (of two different strains of the same species, of two different species of the same genus or of two different species of different genera) according to the alternative embodiment of the invention provides chimeric enzymes which can have unexpected substrate spectra and/or substrate specificity. Without being bound by theory, the change of the substrate spectrum and/or the substrate specificity of such chimeric enzymes compared to the non-chimeric enzymes can be a result from the grouping of subunits from two different organisms. This grouping can e.g. result in a change of the size and/or the sterical accessibility of the reaction center and/or the binding pocket(s) for the substrate(s) of a chimeric enzyme compared to the non-chimeric enzymes. This all holds true for combinations of α and β subunits from different organisms wherein both α and β subunits are disclosed for the first time in accordance with this invention as well as for those embodiments where only one subunit is provided by the present invention and the second one is provided by the prior art. Appropriate tests for assessing the desired specificity etc. are referred to throughout this specification.

All the following preferred and alternative embodiment of the invention refer to the above described embodiments of the polynucleotides or pairs of polynucleotides of the invention.

As described herein above, in a more preferred embodiment of the polynucleotide or pair of polynucleotides of the invention all thymidine residues are replaced by uridine residues. According to this preferred embodiment the polynucleotide or pair of polynucleotides is/are (a) RNA.

As further described herein above, it is also preferred that the polynucleotide or pair of polynucleotides of the invention is/are characterized by a substitution of the sugar-phosphate backbone by a peptide backbone. According to this preferred embodiment the polynucleotide or pair of polynucleotides is/are (a) PNA.

As already described herein above, it is further preferred that the polynucleotide or pair of polynucleotides of the invention is/are DNA, including genomic DNA.

In a further preferred embodiment of the invention at least one of the coding regions for the α- or the β-subunit of the polynucleotide or pair of polynucleotides is fused with a heterologous or homologous polynucleotide. This heterologous or homologous polynucleotide may or may not be or comprise a coding region.

The polynucleotide and/or the encoded enzyme having NHase activity is/are either heterologous with respect to the host or is/are homologous with respect to the host but located in a different genomic environment than the naturally occurring counterpart of said nucleotide sequence. A polynucleotide is "heterologous" when it is derived from a cell or organism belonging to a different strain (preferably to a different species) with regard to the origin of the sequence encoding the α- or β-subunit of the NHase. In contrast, a polynucleotide is "homologous" when it is derived from the same cell or organism as the sequence encoding the α- or β-subunit of the NHase of the invention. "Homologous" with respect to the host but located in a different genomic environment than the naturally occurring counterpart of said nucleotide sequence means that, if the nucleotide sequence is homologous with respect to the host (i.e. is naturally present in the same strain or species), it is not located in its natural location in the genome of said host. In particular it may be surrounded by different genes. In this case the nucleotide sequence may be either under the control of its own promoter or under the control of a heterologous promoter. The location of the introduced nucleic acid molecule can be determined by the skilled person by using methods well-known in the art, including Southern blotting. The polynucleotide(s) according to the invention which is/are present in the host may either be integrated into the genome of the host or be maintained extra-chromosomally. With respect to the first option, it is also to be understood that the polynucleotide or pairs of polynucleotides of the invention can be used to restore or create a mutant gene via homologous recombination.

In a preferred embodiment the heterologous or homologous polynucleotide encodes a polypeptide. An example of a homologous polypeptide is the P16K polypeptide/protein (albeit this protein is in the construct of the invention located in a different position relative to the α or β coding sequence as compared to the natural situation). As described herein above, the P16K protein is an example for an activator derived from *Brevibacterium linens*, strain 32B.1. As also described herein above, such activators are supposed to be involved in the incorporation of the cofactor into the active site of some NHases. According to a further preferred embodiment of the invention the polypeptide encoded by the heterologous polynucleotide is the P16K activator or a functional fragment thereof.

Preferably, the polynucleotide or pair of polynucleotides of the present invention is part of a vector or a pair of vectors. In the case of a pair of vectors, it is preferred that one of the pair of polynucleotides is inserted into one vector whereas the second polynucleotide is inserted into a second vector. Such a vector may be, e.g., a plasmid, cosmid, virus, bacteriophage or another vector used e.g. conventionally in genetic engineering.

The polynucleotide or the pair of polynucleotides of the present invention may be inserted into several commercially available vectors. Non-limiting examples include prokaryotic plasmid vectors, such as the pUC-series, pBluescript (Stratagene), the pET-series of expression vectors including the pETduet-vectors (Novagen) or pCRTOPO (Invitrogen) and vectors compatible with an expression in mammalian cells like pREP (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). The use of yeast expression systems for the expression of a prokaryotic NHase has been e.g. described for the methylotropic yeast *Pichia pastoris* [33]. Examples for plasmid vectors suitable for *Pichia pastoris* comprise e.g. the plasmids pAO815, pPIC9K and pPIC3.5K (all Intvitrogen).

The polynucleotide or the pair of polynucleotides of the present invention referred to above may also be inserted into vectors such that a translational fusion with another polynucleotide is generated. The other polynucleotide may encode a protein which may e.g. increase the solubility and/or facilitate the purification of the fusion protein. Non-limiting examples include pET32, pET41, pET43.

For vector modification techniques, see Sambrook and Russel (2001), loc. cit. Generally, vectors can contain one or more origin of replication (ori) and inheritance systems for cloning or expression, one or more markers for selection in the host, e.g., antibiotic resistance, and one or more expression cassettes.

Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the polynucleotide or pair of polynucleotides of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Possible examples for regulatory elements ensuring the initiation of transcription comprise the cytomegalovirus (CMV) promoter, SV40-promoter, RSV-promoter (Rous sarcome virus), the lacZ promoter, the gai10 promoter, human elongation factor 1α-promoter, CMV enhancer, CaM-kinase promoter, the *Autographa californica* multiple nuclear polyhedrosis virus (AcMNPV) polyhedral promoter or the SV40-enhancer. For the expression in prokaryotes, a multitude of promoters including, for example, the tac-lac-promoter, the lacUV5 or the trp promoter, has been described. Examples for further regulatory elements in prokaryotes and eukaryotic cells comprise transcription termination signals, such as SV40-poly-A site or the tk-poly-A site or the SV40, lacZ and AcMNPV polyhedral polyadenylation signals, downstream of the polynucleotide.

Furthermore, it is preferred that the vector of the invention comprises a selectable marker. Examples of selectable markers include neomycin, ampicillin, and hygromycin resistance and the like. Specifically-designed vectors allow the shuttling of DNA between different hosts, such as bacteria-fungal cells or bacteria-animal cells.

An expression vector according to this invention is capable of directing the replication, and the expression, of the polynucleotide or pair of polynucleotides and encoded enzyme of this invention. Suitable expression vectors which comprise the described regulatory elements are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11, pJOE, the pBBR1-MCS-series, pJB861, pBSMuL, pBC2, pUCPKS, pTACT1 or, preferably, the pET vector (Novagen).

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on vaccinia virus or Semliki Forest Virus can be used as eukaryotic expression system for the nucleic acid molecules of the invention.

The present invention in addition relates to a host genetically engineered with the polynucleotide or pairs of polynucleotides of the invention or with a vector of the invention. Said host may be produced by introducing said polynucleotide or pair of polynucleotides or vector(s) into a host which upon its/their presence mediates the expression of the enzyme having NHase activity.

The host may be any prokaryote or eukaryotic cell. Suitable prokaryotes/bacteria are those generally used for cloning like E. coli (e.g., E. coli strains HB101, DH5α, XL1 Blue, Y1090 and JM101), Salmonella typhimurium, Serratia marcescens, Pseudomonas putida, Pseudomonas fluorescens, Streptomyces lividans, Lactococcus lactis, Mycobacterium smegmatis or Bacillus subtilis. A suitable eukaryotic host may be a mammalian cell, an amphibian cell, a fish cell, an insect cell, a fungal cell or a plant cell. Preferred examples for hosts to be genetically engineered with the polynucleotid or pair of polypeptidenucleotids of the invention are E. coli and Rhodococcus sp. The use of Rhodococcus sp. as host for recombinant expression of nucleic acid sequences is described e.g. in Mizunashi, W. et al. (Appl Microbiol Biotechnol. (1998) 49(5):568-72).

In another embodiment, the present invention relates to a process for producing a pair of polypeptides, forming heteromultimers, or a fusion protein having nitrile hydratase (NHase) [E.C. 4.2.1.84] activity and consisting of or comprising (an) α- and (a) β-subunit(s) as described herein above, the process comprising culturing the host of the invention and recovering the pair of polypeptides or the fusion protein encoded by the polynucleotide or pairs of polynucleotides of the invention.

The term "fusion protein" defines in the context of the invention an artificial protein retaining or essentially retaining NHase activity comprising at least two subunits comprised in a single amino acid chain which do not naturally occur as a single amino acid chain. A fusion protein according to the invention comprises at least one subunit which is a polypeptide of an α- or a β-subunit of an enzyme having NHase activity. The fusion protein may comprise as an/the additional subunit a polypeptide or a peptide, which is fused to the polypeptide of the α- or a β-subunit. This other polypeptide or peptide ("fusion partner"), may e.g. increase the solubility or facilitate the purification of the fusion protein. In another sense the "fusion protein" comprises the α- and β-subunit of an enzyme having NHase activity in a single amino acid chain. The subunits may be connected via a peptide sequence which functions as a "linker". In line with the above, the linker is not naturally part of the polypeptide of either subunit. The linker may allow for a functional formation of the subunits of the NHase, i.e. allow for the formation of a functional enzyme.

A fusion protein is preferably produced by ligation of the polynucleotides encoding the subunits and forming a single coding region comprising the coding regions for both subunits in a single uninterrupted reading frame.

A large number of suitable methods exist in the art to produce polypeptides (or fusion proteins) in appropriate hosts. If the host is a unicellular organism such as a prokaryote, a mammalian or insect cell, the person skilled in the art can revert to a variety of culture conditions. Conveniently, the produced protein is harvested from the culture medium, lysates of the cultured organisms or from isolated (biological) membranes by established techniques. In the case of a multicellular organism, the host may be a cell which is part of or derived from a part of the organism, for example said host cell may be the harvestable part of a plant. A preferred method involves the recombinant production of protein in hosts as indicated above. For example, nucleotide acid sequences comprising the polynucleotide or pair of polynucleotides according to the invention can be synthesized by PCR, inserted into an expression vector. Subsequently a suitable host may be transformed with the expression vector. Thereafter, the host is cultured to produce the desired polypeptide(s), which is/are isolated and purified.

An alternative method for producing the NHase of the invention is in vitro translation of mRNA. Suitable cell-free expression systems for use in accordance with the present invention include rabbit reticulocyte lysate, wheat germ extract, canine pancreatic microsomal membranes, E. coli S30 extract, and coupled transcription/translation systems such as the TNT-system (Promega). These systems allow the expression of recombinant polypeptides upon the addition of cloning vectors, DNA fragments, or RNA sequences containing coding regions and appropriate promoter elements.

In addition to recombinant production, fragments of the protein, the fusion protein or antigenic fragments of the invention may e.g. be produced by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). Synthetic protein synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by Houghton Proc. Natl. Acad. Sci. USA (82) (1985), 5131-5135, can be used.

Protein isolation and purification can be achieved by any one of several known techniques; for example and without limitation, ion exchange chromatography, gel filtration chromatography and affinity chromatography, high pressure liquid chromatography (HPLC), reversed phase HPLC, and preparative disc gel electrophoresis. Protein isolation/purification techniques may require modification of the proteins of the present invention using conventional methods. For example, a histidine tag can be added to the protein to allow purification on a nickel column. Other modifications may cause higher or lower activity, permit higher levels of protein production, or simplify purification of the protein.

The invention also relates in a further alternative embodiment to a process for producing bacteria or eukaryotic cells capable of expressing a pair of polypeptides or a fusion protein having nitrile hydratase (NHase) [E.C. 4.2.1.84] activity and consisting or comprising of (an) α- and (a) β-subunit(s), the process comprising genetically engineering bacteria or eukaryotic cells with the vector of the invention.

Additionally the present invention relates to a pair of polypeptides or a fusion protein comprising the amino acid sequence encoded by a polynucleotide or pair of polynucleotides of the invention or obtainable by the process of the invention. Preferably, the pair of polypeptides or fusion protein of the invention is produced according to the method of the invention. Alternatively, the pair of polypeptides or fusion protein of the invention may be produced synthetically or semisynthetically. In line with the invention the pair of polypeptides is suitable to form heteromultimers having NHase enzyme activity.

In a further embodiment, the present invention relates to an antibody specifically binding to the pair of polypeptides or fusion protein of the invention. It is preferred that the antibody binds to the polypeptides or fusion protein of the invention in the form having NHase enzyme activity. Thus, it is preferred that the antibody binds to a heterodimer, a heterotetramer or a heteromer of even higher number of pairs of subunits of the pair of polypeptides. In the embodiment of the antibody which specifically binds to the fusion protein of the invention, the antibody specifically binds either to epitopes formed by the α- or the β-subunit of the fusion protein. The antibody may also bind to epitopes formed by the stretch of amino acids including the fusion point of the two heterologous polypeptides. This epitopes are characteristic (unique) for the fusion protein of the invention.

The antibody of the present invention can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. These antibodies can be used, for example, for the immunoprecipitation, affinity purification and immunolocalization of the polypeptides or fusion proteins of the invention as well as for the monitoring of the presence and amount of such polypeptides, for example, in cultures of recombinant prokaryotes or eukaryotic cells or organisms.

The antibody of the invention also includes embodiments such as chimeric, single chain and humanized antibodies, as well as antibody fragments, like, inter alia, Fab fragments. Antibody fragments or derivatives further comprise F(ab')$_2$, Fv or scFv fragments; see, for example, Harlow and Lane (1988) and (1999), loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies specific for polypeptide(s) and fusion proteins of this invention. Also, transgenic animals may be used to express humanized antibodies specific for polypeptides and fusion proteins of this invention. Most preferably, the antibody of this invention is a monoclonal antibody. For the preparation of monoclonal antibodies, any technique which provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of an polypeptide of the invention (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, inter alia, viruses or plasmid vectors.

The antibody described in the context of the invention is capable to specifically bind/interact with an epitope of the polypeptides or fusion protein of the invention. The term "specifically binding/interacting with" as used in accordance with the present invention means that the antibody does not or essentially does not cross-react with an epitope of similar structure. Thus, the antibody does not bind to prior art NHases. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of a protein) but do not or do not essentially bind to any of the other epitope are considered specific for the epitope of interest and thus to be antibodies in accordance with this invention. Corresponding methods are described e.g. in Harlow and Lane, 1988 and 1999, loc cit.

The antibody specifically binds to/interacts with conformational or continuous epitopes which are unique for the polypeptides or fusion protein of the invention. A conformational or discontinuous epitope is characterized for polypeptide antigens by the presence of two or more discrete amino acid residues which are separated in the primary sequence, but come together on the surface of the molecule when the polypeptide folds into the native protein/antigen (Sela, (1969) Science 166, 1365 and Layer, (1990) Cell 61, 553-6). The two or more discrete amino acid residues contributing to the epitope are present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues which are present in a single linear segment of a polypeptide chain.

Furthermore and as has been stated above, the present invention relates to a primer which specifically hybridizes under stringent conditions to a polynucleotide or either one of the pair of polynucleotides of the invention.

The primer is at least 10, more preferably at least 15, further preferably at least 20, furthermore preferably at least 25 nucleotides in length. The term "primer" when used in the present invention means a single-stranded nucleic acid molecule capable of annealing to the nucleic acid molecule of the present invention and thereby being capable of serving as a starting point for amplification or elongation. For an amplification reaction it is preferred that a pair of primers is elected. According to the present invention the term "pair of primers" means a pair of primers that are with respect to a complementary region of a nucleic acid molecule directed in the opposite direction towards each other to enable, for example, amplification by polymerase chain reaction (PCR).

The term "amplifying" refers to repeated copying of a specified sequence of nucleotides resulting in an increase in the amount of said specified sequence of nucleotides and allows the generation of a multitude of identical or essentially identical (i.e. at least 95% more preferred at least 98%, even more preferred at least 99% and most preferred at least 99.5% such as 99.9% identical) nucleic acid molecules or parts thereof. Such methods are well established in the art; see Sambrook et al. "Molecular Cloning, A Laboratory Manual", 2nd edition 1989, CSH Press, Cold Spring Harbor. They include polymerase chain reaction (PCR) and modifications thereof, ligase chain reaction (LCR) to name some preferred amplification methods.

It is also preferred that the nucleic acid molecule of the invention is labeled. The label may, for example, be a radioactive label, such as $^{32}P$, $^{33}P$ or $^{35}S$. In a preferred embodiment of the invention, the label is a non-radioactive label, for example, digoxigenin, biotin and fluorescence dye or a dye.

In yet another embodiment, the present invention relates to a composition comprising the polynucleotide or pair of polynucleotide, the pair of polypeptides or fusion protein, the antibody and/or one or more primers of the invention.

The term "composition", as used in accordance with the present invention, relates to a composition which comprise at least one of the recited compounds. It may, optionally, comprises further molecules capable of altering the characteristics of the compounds of the invention thereby, for example, suppressing, stabilizing, blocking, modulating and/or activating their function. The composition may be in solid, liquid or gaseous form and may be, inter alia, in the form of (a) powder(s), (a) tablet(s), (a) solution(s) or (an) aerosol(s).

In a further embodiment the invention relates to a method for the production of amides comprising the enantioselective conversion of nitriles by a heteromultimer, formed by the pair of polypeptides, or a fusion protein according to the invention. A corresponding process is exemplified in the appended example 9.

It is particularly preferred for the method for the production of amides according to the invention that the racemic amygdalic nitrile is converted into (S)-amygdalic amide.

The figures show:

FIG. 1:
Seq ID NO: 1 (*Raoultella terrigena*, strain 77.1) α-subunit

FIG. 2:
Seq ID NO: 2 (*Raoultella terrigena*, strain 77.1) α-subunit

FIG. 3:
Seq ID NO: 3 (*Raoultella terrigena*, strain 77.1) β-subunit

FIG. 4:
Seq ID NO: 4 (*Raoultella terrigena*, strain 77.1) β-subunit

FIG. 5:
Seq ID NO: 5 (*Raoultella terrigena*, strain 37.1) α-subunit

FIG. 6:
Seq ID NO: 6 (*Raoultella terrigena*, strain 37.1) α-subunit

FIG. 7:
Seq ID NO: 7 (*Raoultella terrigena*, strain 37.1) β-subunit

FIG. 8:
Seq ID NO: 8 (*Raoultella terrigena*, strain 37.1) β-subunit

FIG. 9:
Seq ID NO: 9 (*Pantoea* sp., strain 17.3.1) α-subunit

FIG. 10:
Seq ID NO: 10 (*Pantoea* sp., strain 17.3.1) α-subunit

FIG. 11:
Seq ID NO: 11 (*Pantoea* sp., strain 17.3.1) β-subunit

FIG. 12:
Seq ID NO: 12 (*Pantoea* sp., strain 17.3.1) β-subunit

FIG. 13:
Seq ID NO: 13 (*Brevibacterium linens*, strain 32B.1) α-subunit

FIG. 14:
Seq ID NO: 14 (*Brevibacterium linens*, strain 32B.1) α-subunit

FIG. 15:
Seq ID NO: 15 (*Brevibacterium linens*, strain 32B.1) β-subunit

FIG. 16:
Seq ID NO: 16 (*Brevibacterium linens*, strain 32B.1) β-subunit

FIG. 17:
Seq ID NO: 17 (*Klebsiella oxytoca*, strain 38.1.2) α-subunit

FIG. 18:
Seq ID NO: 18 (*Klebsiella oxytoca*, strain 38.1.2) α-subunit

FIG. 19:
Seq ID NO: 19 (*Klebsiella oxytoca*, strain 38.1.2) β-subunit

FIG. 20:
Seq ID NO: 20 (*Klebsiella oxytoca*, strain 38.1.2) β-subunit

FIG. 21:
Seq ID No. 21 (*Brevibacterium linens*, strain 32B.1) P16K

FIG. 22:
Seq ID No. 21 (*Brevibacterium linens*, strain 32B.1) P16K

FIG. 23:
Dependence of the activity of the NHase according to Seq ID No. 2 and 4 (*Raoultella terrigena*, 77.1) on the temperature.

As enzyme samples cell free crude extracts were used either of the heterologously or homologously produced enzyme. The substrate (1 mM 2-phenylpropionitrile (PPN) in 50 mM Tris/HCl pH 7.5)) was equilibrated at the indicated temperatures before the reaction was started by addition of 50 µl of enzyme sample. The activity was determined as described in example 4.

FIG. 24:
Dependence of the activity of the NHase according to Seq ID No. 18 and 20 (*Klebsiella oxytoca*, 38.1.2) on the temperature.

As enzyme samples lyophilized cells or a cell free crude extract were used. The samples were equilibrated for 5 min at the indicated temperatures before the reaction was started by addition of PPN to a final concentration of 1 mM. The activity was determined as described in example 4.

Figure 25:
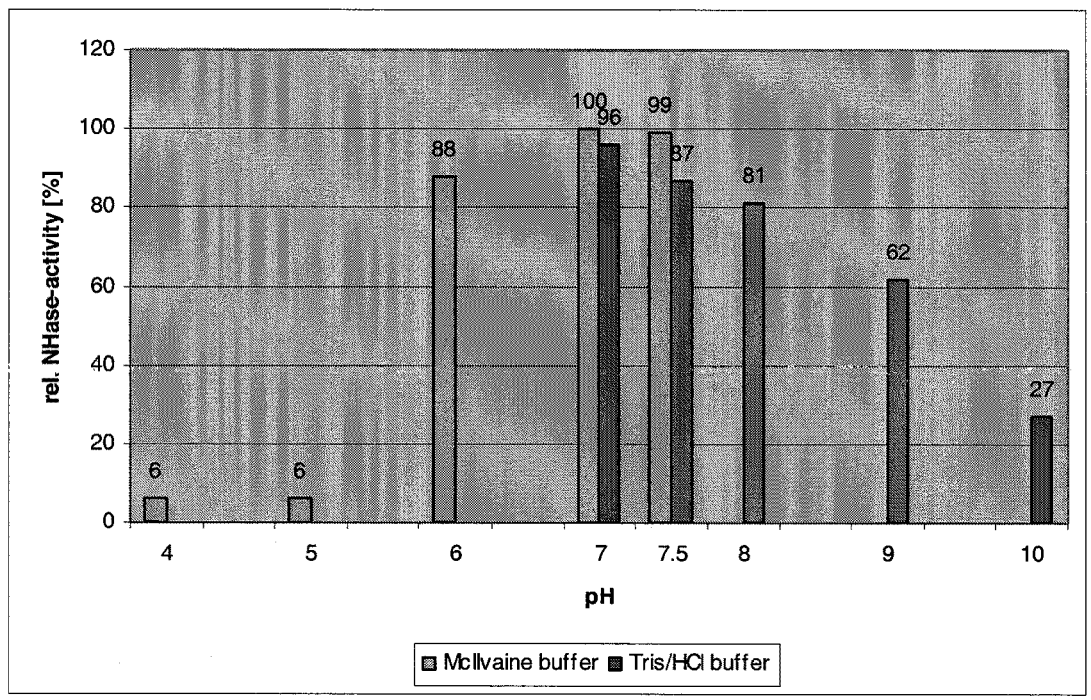

FIG. 25:
Dependence of the activity of the NHase according to Seq ID No. 2 and 4 (*Raoultella terrigena*, 77.1) on the pH.

Cell free crude extracts from *Raoultella terrigena* (77.1) were incubated for 5 min at 30° C. and the indicated pH-values. The reaction was subsequently started by addition of substrate (1 mM PPN). The activity was determined as described in example 4. Buffers used: McIlvaine buffer: ~0.1 M citrate/phosphate-buffer; Tris-buffer: 0.1 M Tris/HCl-buffer FIG. 26:
Dependence of the activity of the NHase according to Seq ID No. 2 and 4 (*Raoultella terrigena*, 77.1) on the pH.

Cell free crude extracts from *E. coli* BL21 (DE3) pET22_77.1a/pET26_77.1b were incubated for 5 min at 30° C. and the indicated pH-values. The reaction was subsequently started by addition of substrate (1 mM PPN). The activity was determined as described in example 4. Buffers used: McIlvaine buffer: ~0.1 M citrate/phosphate-buffer; Tris-buffer: 0.1 M Tris/HCl-buffer FIG. 27:
Dependence of the activity of the NHase according to Seq ID No. 2 and 4 (*Raoultella terrigena*, 77.1) on the pH.

Cell free crude extracts from *Klebsiella* sp. (77.1) and *E. coli* BL21 (DE3) pET22_77.1a/pET26_77.1b were incubated for 5 min at 30° C. and the indicated pH-values. The reaction was subsequently started by addition of substrate (1 mM PPN). The activity was determined as described in example 4. Buffers used: McIlvaine buffer: ~0.1 M citrate/phosphate-buffer FIG. 28:
Dependence of the activity of the NHase according to Seq ID No. 18 and 20 (*Klebsiella oxytoca*, 38.1.2) on the pH.

Lyophilized cells were incubated for 5 min at the indicated pH-values. The reaction was subsequently started by addition of substrate (1 mM PPN). The activity was determined as described in example 4. Buffers used: McIlvaine buffer: ~0.1 M citrate/phosphate-buffer; Tris-buffer: 0.1 M Tris/HCl-buffer

FIG. 29:

Dependence of the activity of the NHase according to Seq ID No. 18 and 20 (*Klebsiella oxytoca*, 38.1.2) on the pH.

Cell free crude extracts were incubated for 5 min at the indicated pH-values. The reaction was subsequently started by addition of substrate (1 mM PPN). The activity was determined as described in example 4. Buffers used: McIlvaine buffer: ~0.1 M citrate/phosphate-buffer; Tris-buffer: 0.1 M Tris/HCl-buffer The invention will now be described by reference to the following examples which are merely illustrative and are not to be construed as a limitation of scope of the present invention.

EXAMPLE 1

Material for the Screening for NHase Activity

For the isolation of the NHase-producing strains a minimal medium containing the following compounds per liter was used: $KH_2PO_4$ (1.4 g), $Na_2HPO_4$ (7.0 g), fructose (5.0 g), iron (III) citrate (20 mg), $MgSO_4.7H_2O$ (1.0 g), $CaCl_2.2H_2O$ (50 mg) SL6 (1 ml, 1000×; 1000×SL6 is composed of $ZnCl_2$ 70 mg; $MnCl_2×4H_2O$ 100 mg; $H_3BO_3$ 62 mg; $CoCl_2×6H_2O$ 190 mg; $CuCl_2×2H_2O$ 17 mg; $NiCl_2×6H_2O$ 24 mg; $Na_2MoO4×2H_2O$ 36 mg; HCl (25%) 1.3 mL ad 1 l $H_2O$) and 2-phenylpropionitrile (100 mM in MeOH, 10 ml) was added. Samples from different habitates were used to inoculate the minimal medium.

EXAMPLE 2

Identification of the Genes Encoding the Subunits of Nitrile Hydratases

By the use of degenerate oligonucleotides designed to target sequences encoding conserved structural motifs in the α-subunits of NHases sequence tags were amplified from the genomic DNA of the strains isolated as described above. The PCR reactions were performed with 100 ng of genomic DNA, 10 pmol each of forward and reverse primer, 200 µM of each dNTP and 2.5 U of Taq polymerase, e.g. the HotStarTaq-Polymerase (Qiagen), in a 50 µl volume of buffer provided by the manufacturer of the polymerase. Following one initial denaturation step (15 min at 95° C.), 35 cycles of amplification (30 sec at 95° C., 1 min at 55° C.-65° C., 1 min at 72° C.) and a final elongation step (7 min at 72° C.) were carried out. PCR-products were cloned and sequenced by techniques known to persons in the state of the art. To determine the full length sequence of the genes encoding the α- and the β-subunits, genomic libraries were constructed for each of the identified strain in *E. coli*. Clones from the libraries carrying the genes encoding the nitrile hydratases were identified by a PCR-screening using specific primers derived from the sequence-tags. The determination of the full length sequence was performed by techniques known to persons in the state of the art. For the construction of the expression constructs, the corresponding NHase genes were PCR amplified to introduce unique restriction enzyme recognition sequences upstream and downstream of the open reading frame (ORF) which allowed to ligate the genes encoding the NHases to the expression vector in a definite way. The restriction enzyme recognition sequences were chosen on the basis of their absence in the coding region of the NHase genes and could be e.g. NdeI, XhoI. The absence of unwanted second site mutations due to erroneous amplification by the polymerase was confirmed by sequencing of the cloned amplicons. The genes encoding the α- and the β-subunits were amplified separately.

EXAMPLE 3

Heterologous Expression of NHases

The amplified α-subunits were ligated to pET22b whereas the β-subunits were ligated to pET26b by use of the unique NdeI and XhoI restriction enzyme recognition sites. *E. coli* BL21 (DE3) or *E. coli* Rosetta (DE3) was cotransformed with the vectors carrying the genes for the corresponding α- and β-subunits of the NHases. Freshly transformed cells were grown over night at 37° C. in 5 ml LB-medium containing 100 µg/ml ampicillin, 25 µg/ml kanamycin and 2% (w/v) glucose. In case of *E. coli* Rosetta (DE3) 12.5 µg/ml chloramphenicol was additionally used. 1 ml of this culture was used to inoculate 100 ml of LB-medium containing 100 µg/ml ampicillin, 25 µg/ml kanamycin and 1% (w/v) glucose. Cells were incubated at 20° C. or 30° C. on a gyratory shaker at 100 rpm. At an optical density $O.D._{595}=1$ cells were induced by addition of 100 µg/ml IPTG. Simultaneously, $CoCl_2*6H_2O$ was added in a concentration of 250 µM. When the P16K activator protein from the strain *Brevibacterium linens* was coexpressed with the corresponding NHase *E. coli* Rosetta (DE3) pET22_32B1α pET26_32B.1β pBBR5_32B_P16K was grown in LB-medium containing 100 µg/ml ampicillin, 25 µg/ml kanamycin, 12.5 µg/ml chloramphenicol and 10 µg/ml gentamycin and 1% (w/v) glucose. Samples were taken 24 h after induction.

EXAMPLE 4

Determination of Enzyme Activity

If not otherwise indicated enzyme samples were prepared as follows: the cells from 1 ml of the culture were washed with 50 mM Tris/HCl pH 7.5 and resuspended in 750 µl of the same buffer. This suspension was incubated at 30° C. in a thermomixer at 1000 rpm. The biotransformation was started by addition of the substrate 2-phenylpropionitrile (PPN) in 50 mM Tris/HCl pH 7.5. The concentration of the substrate was 1 mM, if not otherwise stated. The reaction was stopped after 1 min, 5 min or 10 min as indicated by addition of 1 M HCl. Cells were removed by centrifugation and the supernatant analysed by HPLC for the presence of the corresponding amide. The HPLC analysis was carried out on a system comprising a Surveyor 4 channel Pump, AutoSampler and UVNIS detector at 210 nm from Thermo Finnigan on a Grom-Sil 1200DS-3 cp 3 µm (125×4.6 mm) reverse phase column. As mobile phase, acetonitrile and 0.3% $H_3PO_4$ were used in a ratio of 50:50 at a flow of 0.7 ml/min, respectively.

The activity of the NHases towards PPN is given in Table 15.

EXAMPLE 5

Determination of Enantioselectivity

For the determination of enantioselectivity towards rac-mandelonitrile and 2-phenylpropionitrile 40-50 mg of washed cells were resuspended in 1 ml of 50 mM Tris/HCl pH 7.5. 100 µl of cell suspension were mixed with 800 µl 50 mM Tris/HCl pH 7.5 and incubated at 30° C. in a thermomixer at 1000 rpm. The biotransformation was started by addition of 100 µl of 10 mM rac-mandelonitrile or rac-2-phenylpropionitrile in 50 mM Tris/HCl pH 7.5. The reaction was stopped by addition of 100 µl 1M HCl after 1, 5 or 10 min. Cells were removed by centrifugation and the supernatant analysed by chiral HPLC for the presence of mandeloamide and phenylpropionamide, respectively. rac-Mandeloamide was analysed on a HPLC comprising a Surveyor 4 channel Pump, AutoSampler and UVNIS detector at 210 nm from Thermo Finnigan on a Nucleodex β-OH column (Macherey & Nagel) using 50% methanol/water:water (40:60) as mobile phase at a flow rate of 0.7 ml/min. The apparent enantiomeric ratio ($E_{app}$) of the conversion of mandelonitrile was calculated according to Straathof and Jongejan for asymmetric catalysis (see example 9). In case of 2-phenylpropionamide, the samples were lyophilized and resuspended in n-hexane: 2-propanol (80:20). Prior to injection, the samples were additionally dried with sodium sulfate and were centrifugated at 16,000 g for 5 min. The supernatants were analyzed using a Chiracel OD column (Daicel) on a Spectra System (AS3000, P2000, UV2000 at 210 nm) from Thermo Separation Products with n-hexane: 2-propanol (80:20) as mobile phase at a flow rate of 0.5 ml/min. The enantiomeric ratio (E) of the conversion of PPN was calculated according to Chen et al [17].

All enzymes showed a preference for the (S)-enantiomer of mandelonitrile and the (S)-enantiomer of 2-phenylpropionitrile. The enantiomeric excess (ee %) and the enantioselectivity are given in Tables 13 and 14, respectively.

For the enzyme according Seq ID No. 2 and 4 (*Raoultella terrigena*, 77.1) and Seq ID. No. 18 and 20 (*Klebsiella oxytoca*, 38.1.2) the substrate spectrum was determined. Relative activities towards a variety of substrates are given in Table 16. The activities were compared to the activity towards 2-phenylpropionitrile which was set to 100%. Both enzymes are capable of the conversion of aliphatic as well as aromatic substrates.

EXAMPLE 6

Determination of the Temperature Optimum

The optimal temperatures for the NHases according to Seq ID No. 2 and 4 (*Raoultella terrigena*, 77.1) and Seq ID. No. 18 and 20 (*Klebsiella oxytoca*, 38.1.2) were determined to be at 45° C. (FIG. 23 and FIG. 24). At 55° C. a residual activity of about 20% was found for the enzyme according to Seq ID-No. 18 and 20 whereas at 60° C. no activity could be determined. However the enzyme according to Seq ID No. 2 and 4 showed a residual activity at 60° C. of 60-79%

EXAMPLE 7

Determination of the pH-Optimum

Figure 26:
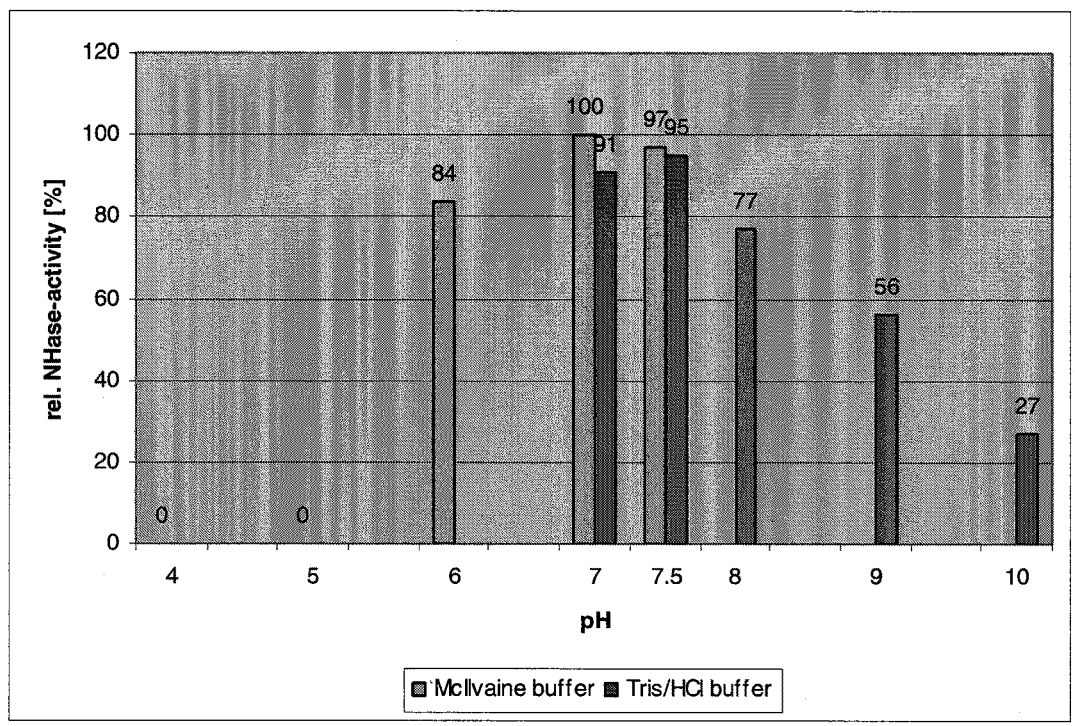
Figure 27:
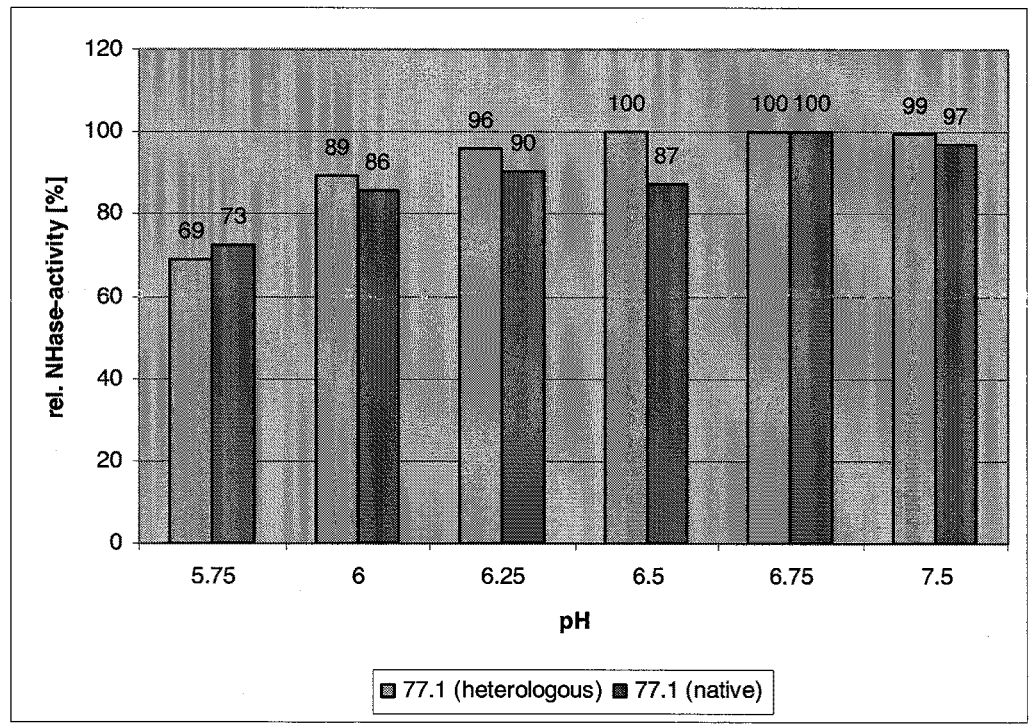

The pH-optimum for the enzyme according to Seq ID No. 2 and 4 (*Raoultella terrigena*, 77.1) has its pH-optimum at pH 6.75 (FIG. 27). Whereas the recombinantly produced enzyme showed no activity at a pH<6.0 the homologously produced enzyme displays a residual activity of about 6% at pH 4.0. Both enzyme preparations had a residual activity of about 27% at pH 10.0 (FIGS. 25 and 26)

Figure 28:
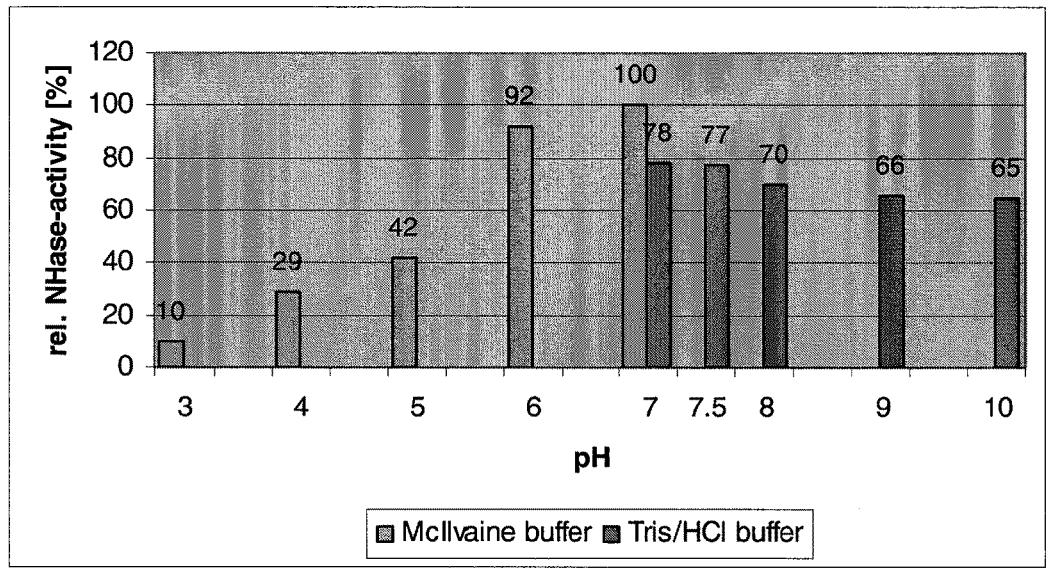
Figure 29:
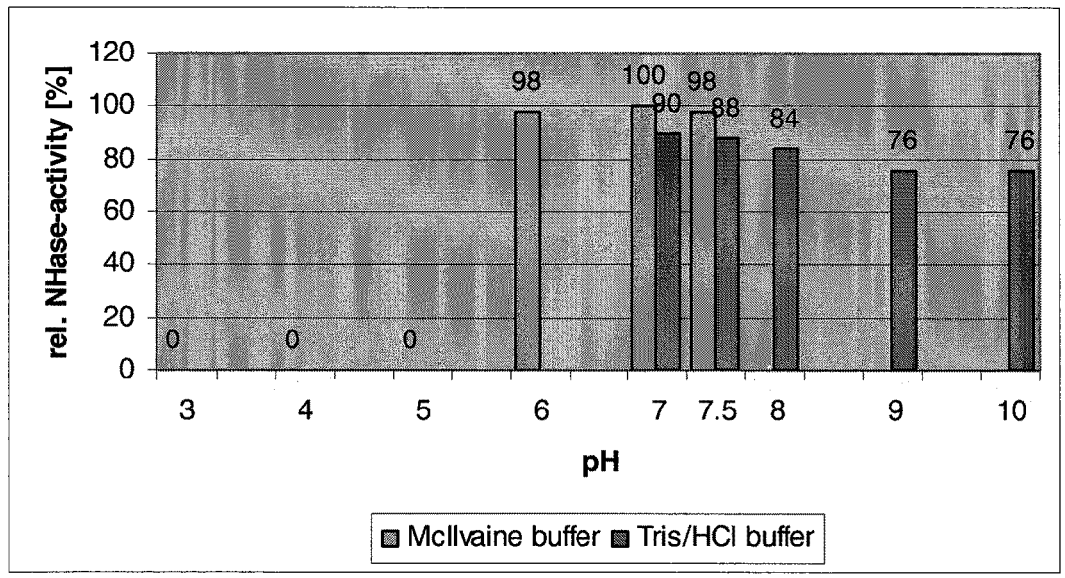

The NHase according to Seq ID. No. 18 and 20 (*Klebsiella oxytoca*, 38.1.2) was determined to be between pH 7.0-pH 7.5 (FIG. 28 and FIG. 29). When using crude cell extracts as enzyme samples the enzyme is inactivated at a pH-value<6 whereas lyophilized cells showed a residual activity of about 10% even at pH 3.0. At a pH 10, the residual activity of the enzyme is about 65-75%.

EXAMPLE 8

Determination of the Isoelectric Point (IEP)

The IEP of the purified enzyme according to Seq. ID No. 2 and 4 was determined to be 3.5-3.6 using the Phast-System (Amersham Pharmacia).

EXAMPLE 9

A Process for the Enantioselective Conversion of Mandelonitrile

For the hydrolysis of rac-mandelonitrile washed cells or cell free crude extract having nitrile hydratase activity could be used. The heterologous expression of NHase is described in Example 3.

Washed cells are resuspended in 50 mM $Na_2HPO_4$/$KH_2PO_4$ pH 7.5. The reaction is started by addition of mandelonitrile to a final concentration of 1 mM. The biotransformation is performed at 30° C.

Due to the instability of mandelonitrile and reverse chemical reaction of benzaldehyde with cyanide in phosphate buffer to form rac-mandelonitrile, a theoretically 100% yield of enantiopure mandeloamide is possible by asymmetric catalysis.

List of Tables

TABLE 1 nitrile hydratases with enantiopreference for the given substrate

| strain | substrate | enantio-preference | reference |
|---|---|---|---|
| *P. putida* 5B | 2-(4-chlorophenyl)-3-methylbutyronitrile | S | [34, 4] |
| *P. putida* 5B | 2-(6-methoxy-2-naphtyl)-propionitrile | R | [38] |
| *P. putida* 13-5S-ACN-2a | 2-(4-isobutylphenyl)propionitrile | R | [13, 16] |
| *P. putida* 5B-MNG-2P | 2-(4-chlorophenyl)-3-methylbutyronitrile | S | [13, 16] |
| *P. putida* 5B-MNG-2P | 2-(4-isobutylphenyl)propionitrile | R | [13, 16] |
| *P. putida* 5B-MNG-2P | 2-(6-methoxy-2-naphtyl)-propionitrile | R | [13, 16] |
| *Pseudomonas* species 2D-11-5-1c | 2-(6-methoxy-2-naphtyl)-propionitrile | S | [13, 16] |
| *Pseudomonas* species 2G-8-5-1a | 2-(6-methoxy-2-naphtyl)-propionitrile | S | [13, 16] |

TABLE 1-continued nitrile hydratases with enantiopreference for the given substrate

| strain | substrate | enantio-preference | reference |
|---|---|---|---|
| *Pseudomonas* species 3L-G-1-5-1a | 2-(6-methoxy-2-naphtyl)-propionitrile | S | [13, 16] |
| *P. aureofaciens* MOB C2-1 | 2-(6-methoxy-2-naphtyl)-propionitrile | R | [13, 16] |
| *P. aureofaciens* MOB C2-1 | 2-(4-isobutylphenyl)-propionitrile | S | [13, 16] |
| *A. tumefaciens* d3 | ketoprufen nitrile | S | [35] |
| *Moraxella* species 3L-A-1-5-1a-1 | 2-(4-chlorophenyl)-3-methylbutyronitrile | S | [13, 16] |
| *Moraxella* species 3L-A-1-5-1a-1 | 2-(4-isobutylphenyl)propionitrile | R | [13, 16] |
| *Serratia liquefaciens* MOB/IM/N3 | 2-(4-chlorophenyl)-3-methylbutyronitrile | S | [13, 16] |
| *Rhodococcus* sp. AJ270 | 2-phenylbutyronitrile | R | [36] |
| *Rhodococcus* sp. HT40-6 | mandelonitrile | S | [37] |
| *P. putida* 5B | 2-(4-chlorophenyl)-3-methylbutyronitrile | S | [34, 4] |

TABLE 2

Enantioselective nitrile hydratases

| strain | substrate | enantio-preference | enantio-selectivity [E] | reference |
|---|---|---|---|---|
| *P. putida* 2D-11-5-1b | 2-(4-chlorophenyl)-3-metyhlbutyronitrile | S | ca. 63 | [13, 16] |
| *P. putida* 2D-11-5-1b | 2-(4-isobutylphenyl)-propionitrile | R | ca. 13 | [13, 16] |
| *P. putida* 13-5S-ACN-2a | 2-(4-chlorophenyl)-3-metyhlbutyronitrile | S | ca. 48 | [[13, 16] |
| *A. tumefaciens* d3 | 2-phenylpropionitrile | S | 253 | [13, 35, 39] |
| *A. tumefaciens* d3 | 2-phenylbutyronitrile | S | 58 | [13, 35, 39] |
| *A. tumefaciens* d3 | 3-(Bz)Ph-propionitrile | S | 43 | [13, 39] |
| *A. tumefaciens* d3 | 2-(4-chlorophenyl)-3-propionitrile | S | 18 | [13, 35, 39] |
| *A. tumefaciens* d3 | 2-(4-methoxyphenyl)-3-propionitrile | S | 8 | [13, 35, 39] |
| *Rhodococcus equi* A4 | 2-(6-methoxy-2-naphtyl)propionitrile | S | 41 | [40] |
| *Rhodococcus equi* A4 | 2-(4-methoxyphenyl)-3-propionitrile | S | 19 | [40] |
| *Rhodococcus equi* A4 | 2-(2-methoxyphenyl)-3-propionitrile | S | 7 | [40] |
| *Rhodococcus equi* A4 | 2-(4-chlorophenyl)-3-propionitrile | S | 5 | [40] |

TABLE 3

Sequence identity of the enzyme according to Seq Id No. 1
(*Raoultella terrigena*, strain 77.1 α-subunit)

| next neighbour | gene identifier | organism | identity | overlap | reference |
|---|---|---|---|---|---|
| nitrile hydratase alpha subunit | E08305 | *Klebsiella* sp. MCI2609 | 85.9% | 609 bp | [42] |
| nitrile hydratase alpha subunit | AJ971318 | *Agrobacterium tumefaciens* | 74.6% | 579 bp | Lourenco P.M.L. unpublished |
| nitrile hydratase alpha subunit | BX572602 | *Rhodopseudomonas palustris* CGA009 | 70.6% | 603 bp | [43] |

TABLE 3-continued

Sequence identity of the enzyme according to Seq Id No. 1
(*Raoultella terrigena*, strain 77.1 α-subunit)

| next neighbour | gene identifier | organism | identity | overlap | reference |
|---|---|---|---|---|---|
| nitrile hydratase alpha subunit | PPU89363 | *Pseudomonas putida* | 70.1% | 602 bp | [34] |
| nitrile hydratase alpha subunit | AR116601 | Sequence 16 from patent U.S Pat. No. 6,133,421 | 69.8% | 600 bp | [44] |

TABLE 4

Sequence identity of the enzyme according to Seq Id No. 3
(*Raoultella terrigena*, strain 77.1 β-subunit)

| next neighbour | gene identifier | organism | identity | overlap | reference |
|---|---|---|---|---|---|
| nitrile hydratase beta subunit | E08305 | *Klebsiella* sp. MCI2609 | 82.0% | 654 bp | [42] |
| nitrile hydratase beta subunit | AJ971318 | *Agrobacterium tumefaciens* | 66.7% | 664 bp | Lourenco unpublished |
| nitrile hydratase beta subunit | ATU511276 | *Agrobacterium tumefaciens* | 66.8% | 665 bp | Lourenco et al. unpublished |
| nitrile hydratase beta subunit | AY743666 | *Comamonas testosteroni* 5-MGAM-4D | 64.2% | 612 bp | [45] |
| nitrile hydratase beta subunit | CS174944 | Sequence 65 from Patent WO2005090595 | 61.0% | 656 bp | [46] |

TABLE 5

Sequence identity of the enzyme according to Seq Id No. 5
(*Raoultella terrigena*, strain 37.1 α-subunit)

| next neighbour | gene identifier | organism | identity | overlap | reference |
|---|---|---|---|---|---|
| nitrile hydratase alpha subunit | E08305 | *Klebsiella* sp. MCI2609 | 85.7% | 609 bp | [42] |
| nitrile hydratase alpha subunit | AJ971318 | *Agrobacterium tumefaciens* | 75.0% | 579 bp | Lourenco P.M.L. unpublished |
| nitrile hydratase alpha subunit | BX572602 | *Rhodopseudomonas palustris* CGA009 | 70.6% | 603 bp | [43] |
| nitrile hydratase alpha subunit | AY743666 | *Comamonas testosteroni* 5-MGAM-4D | 69.4% | 602 bp | [45] |
| nitrile hydratase alpha subunit | PPU89363 | *Pseudomonas putida* | 69.3% | 603 bp | [34] |

TABLE 6

Sequence identity of the enzyme according to Seq Id No. 7
(*Raoultella terrigena*, strain 37.1 β-subunit)

| next neighbour | gene identifier | organism | identity | overlap | reference |
|---|---|---|---|---|---|
| le hydratase beta subunit | E08305 | *Klebsiella* sp. MCI2609 | 82.9% | 654 bp | [42] |
| nitrile hydratase beta subunit | AJ971318 | *Agrobacterium tumefaciens* | 67.2% | 667 bp | Lourenco unpublished |

TABLE 6-continued

Sequence identity of the enzyme according to Seq Id No. 7
(*Raoultella terrigena*, strain 37.1 β-subunit)

| next neighbour | gene identifier | organism | identity | overlap | reference |
|---|---|---|---|---|---|
| nitrile hydratase beta subunit | ATU511276 | *Agrobacterium tumefaciens* | 67.1% | 668 bp | Lourenco et al. unpublished |
| nitrile hydratase beta subunit | AY743666 | *Comamonas testosteroni* 5-MGAM-4D | 64.2% | 611 bp | [45] |
| nitrile hydratase beta subunit | CS174944 | Sequence 65 from Patent WO2005090595 | 60.8% | 656 bp | [46] |

TABLE 7

Sequence identity of the enzyme according to Seq Id No. 9
(*Pantoea* sp., strain 17.3.1 α-subunit)

| next neighbour | gene identifier | organism | identity | overlap | reference |
|---|---|---|---|---|---|
| nitrile hydratase alpha subunit | CS174936 | Sequence 57 from Patent WO2005090595 | 64.9% | 570 bp | [46] |
| nitrile hydratase alpha subunit | AY743666 | *Comamonas testosteroni* 5-MGAM-4D | 65.4% | 563 bp | [45] |
| nitrile hydratase alpha subunit | CS174920 | Sequence 41 from Patent WO2005090595 | 64.6% | 562 bp | [46] |
| nitrile hydratase alpha subunit | PPU89363 | *Pseudomonas putida* | 63.9%% | 563bp | [34]) |
| nitrile hydratase alpha subunit | AJ971318 | *Agrobacterium tumefaciens* | 64.2% | 561 bp | Lourenco P.M.L. unpublished |

TABLE 8

Sequence identity of the enzyme according to Seq Id No. 11
(*Pantoea* sp., strain 17.3.1 β-subunit)

| next neighbour | gene identifier | organism | identity | overlap | reference |
|---|---|---|---|---|---|
| nitrile hydratase beta subunit | AY743666 | *Comamonas testosteroni* 5-MGAM-4D | 55.5% | 602 bp | [45] |
| nitrile hydratase beta subunit | SME591789 | *Sinorhizobium meliloti* 1021 | 53.7% | 657 bp | [47] |
| nitrile hydratase beta subunit | AJ971318 | *Agrobacterium tumefaciens* | 53.8% | 654 bp | Lourenco P.M.L. unpublished |
| nitrile hydratase beta subunit | ATU511276 | *Agrobacterium tumefaciens* | 53.7% | 654 bp | Lourenco et al. unpublished |
| nitrile hydratase beta subunit | E08305 | *Klebsiella* sp. MCI2609 | 52.9% | 601 bp | [42] |

TABLE 9

Sequence identity of the enzyme according to Seq Id No. 13
(*Brevibacterium linens*, strain 32B.1 α-subunit)

| next neighbour | gene identifier | organism | identity | overlap | reference |
|---|---|---|---|---|---|
| nitrile hydratase alpha subunit | M74531 | *Rhodococcus* sp | 73.6% | 584 bp | [48] |
| nitrile hydratase alpha subunit | E03848 | *Rhodococcus rhodochrous* | 74.2% | 569 bp | [49] |
| nitrile hydratase alpha subunit | CS176720 | *Rhodococcus opacus* | 72.0% | 590 bp | [50] |
| nitrile hydratase alpha subunit | AX538034 | *Rhodococcus* sp. | 73.1% | 568 bp | [51] |
| nitrile hydratase alpha subunit | E28648 | *Pseudonocardia thermophila* | 72.3% | 577 bp | [52] |

TABLE 10

Sequence identity of the enzyme according to Seq Id No. 15
(*Brevibacterium linens*, strain 32B.1 β-subunit)

| next neighbour | gene identifier | organism | identity | overlap | reference |
|---|---|---|---|---|---|
| nitrile hydratase beta subunit | DD029959 | *Pseudonocardia thermophila* | 70.3% | 688 bp | [53] |
| nitrile hydratase beta subunit | M74531 | *Rhodococcus* sp | 67.0% | 713 bp | [48] |
| nitrile hydratase beta subunit | CS176720 | *Rhodococcus opacus* | 65.5% | 693 bp | [50] |
| nitrile hydratase beta subunit | AX538034 | *Rhodococcus* sp. | 62.4% | 681 bp | [51] |
| nitrile hydratase beta subunit | E03848 | *Rhodococcus rhodochrous* | 62.0% | 677 bp | [49] |

TABLE 11

Sequence identity of the enzyme according to Seq Id No. 17
(*Klebsiella oxytoca*, strain 38.1.2 α-subunit)

| next neighbour | gene identifier | organism | identity | overlap | reference |
|---|---|---|---|---|---|
| nitrile hydratase alpha subunit | E08305 | *Klebsiella* sp. MCI2609 | 86.0% | 609 bp | [42] |
| nitrile hydratase alpha subunit | ATU511276 | *Agrobacterium tumefaciens* | 76.3% | 579 bp | Lourenco et al. unpublished |
| nitrile hydratase alpha subunit | PPU89363 | *Pseudomonas putida* | 71.1% | 602 bp | [34] |
| nitrile hydratase alpha subunit | AY743666 | *Comamonas testosteroni* 5-MGAM-4D | 70.9% | 602 bp | [45] |
| nitrile hydratase alpha subunit | AR159944 | unidentified | 71.1% | 598 bp | [54] |

TABLE 12

Sequence identity of the enzyme according to Seq Id No. 19
(*Klebsiella oxytoca*, strain 38.1.2 β-subunit)

| next neighbour | gene identifier | organism | identity | overlap | reference |
|---|---|---|---|---|---|
| nitrile hydratase beta subunit | E08305 | *Klebsiella* sp. MCI2609 | 82.9% | 654 bp | [42] |
| nitrile hydratase beta subunit | AJ971318 | *Agrobacterium tumefaciens* | 66.4% | 664 bp | Lourenco P.M.L. unpublished |
| nitrile hydratase beta subunit | ATU511276 | *Agrobacterium tumefaciens* | 66.7% | 670 bp | Lourenco et al. unpublished |
| nitrile hydratase beta subunit | AY743666 | *Comamonas testosteroni* 5-MGAM-4D | 65.1% | 622 bp | [45] |
| nitrile hydratase beta subunit | CS174944 | Sequence 65 from Patent WO2005090595 | 61.4% | 655 bp | [46] |

TABLE 13

Enantioselectivity of NHases towards rac-mandelonitrile

| strain | NHase (Seq ID No.) | $E_{app}$-value homologously expressed | $E_{app}$-value heterologously expressed |
|---|---|---|---|
| Raoultella terrigena, 77.1 | 2 and 4 | 19 | 20 |
| Raoultella terrigena, 37.1 | 6 and 8 | 17 | 18 |
| Pantoea sp., 17.3.1 | 10 and 12 | 5 | 4 |
| Brevibacterium linens, 32B.1 | 14 and 16 | 4 | 4 |
| Klebsiella oxytoca, 38.1.2 | 18 and 20 | 17 | 19 |

TABLE 14

Enantioselectivity of NHases towards rac-2-phenylpropionitrile

| strain | NHase (Seq ID No.) | E-value |
|---|---|---|
| Raoultella terrigena, 77.1 | 2 and 4 | 47 |
| Raoultella terrigena, 37.1 | 6 and 8 | 47 |
| Pantoea sp., 17.3.1 | 10 and 12 | 2 |
| Brevibacterium linens, 32B.1 | 14 and 16 | 8 |
| Klebsiella oxytoca, 38.1.2 | 18 and 20 | 35 |

TABLE 15

Activity of enzyme samples after heterologous expression of NHases in E. coli towards 1 mM 2-phenyl-propionitrile (PPN). The biotransformation reactions were stopped after 1 min incubation.

| expression vectors | biomass [g cdw/L cultur] | vol. activity [μkat/L cultur] | spec. activity [μkat/g cdw] |
|---|---|---|---|
| pET22__17.3.1a/pET26__17.3.1b[a)] | 1.6 | 0.6 | 0.4 |
| pET22__37.1a/pET26__37.1b[a)] | 2 | 5.5 | 2.8 |
| pET22__38.1.2a/pET26__38.1.2b[a)] | 0.9 | 8.6 | 9.6 |
| pET22__77.1a/pET26__77.1b[a)] | n.d. | 4.9 | n.d. |
| pET22__32B.1a/pET26__32B.1b[b)] | 1.5 | 25.3 | 16.9 |
| pET22__32B.1a/pET26__32B.1b/pBBR__P16K__32B.1[b)] | 1 | 36.7 | 36.7 |

[a)] E. coli BL21 (DE3),
[b)] E. coli Rosetta (DE3),
n.d.: not determined

TABLE 16

Relative activity of NHases from Raoultella terrigena, 77.1 and Kiebsiella oxytoca, 38.1.2 towards different cyanohydrins.

| substrate | Structure | rel. activity [%] 77.1 | rel. activity [%] 38.1.2 |
|---|---|---|---|
| 2-phenyl-propionitrile | (CH₃, phenyl, CN) | 100 | 100 |
| mandelonitrile | (OH, phenyl, CN) | 5 | 9 |
| benzonitrile | (phenyl-CN) | 18 | 25 |
| phenyl-acetonitrile | (phenyl-CH₂-CN) | 1 | 1 |
| 2-phenyl-butyronitrile | (H₃C-CH₂, phenyl, CN) | 1 | 18 |
| phenyl-glycine nitrile | (NH₂, phenyl, CN) | 19 | 17 |
| 3-cyanopyridine | (pyridine-CN) | 21 | n.b. |
| butyronitrile | (CH₃CH₂CH₂CN) | 242 | 281 |
| methacrylonitrile | (CH₃, H₂C=, CN) | 109 | 138 |

Enzyme samples of the NHase from Raoultella terrigena, 77.1 were used as cell free crude cell extracts whereas those from Kiebsiella oxytoca, 38.1.2 were lyophilized cells. 100% activity towards 2-phenyl-propionitrile relates to 2,43 nkat and 4.0 nkat for the NHases from Raoultella terrigena, 77.1 and Kiebsiella oxytoca, 38.1.2, respectively.

REFERENCES

[1] D. A. Cowan et al. Comparative biology of mesophilic and thermophilic nitrile hydratases, *Adv. Appl. Microbiol.*, 2003, 52, 123-158

[2] J. Lu et al. Motif CXCC in nitrile hydratase activator is critical for NHase biogenesis in vivo, *FEBS Lett.*, 2003, 553, 391-396

[3] M. Nojir M et al. Functional expression of nitrile hydratase in *Escherichia coli*: requirement of a nitrile hydratase activator and post-translational modification of a ligand cysteine, *J. Biochem.*, 1999, 125, 696-704

[4] S. Wu et al. Over-production of stereoselective nitrile hydratase from *Pseudomonas putida* 5B in *Escherichia coli*: activity requires a novel downstream protein, *Appl. Microbiol. Biotechnol.*, 1997, 48, 704-708

[5] Y. Kato et al. Distribution of Aldoxime Dehydratase in Microorganisms, *Appl. Envir. Microbiol.*, 2000, 66, 2290-2296.

[6] M. Kobayashi & S. Shimizu, Metalloenzyme nitrile hydratase: structure, regulation, and application to biotechnology, *Nat Biotechnol.*, 1998, 16, 733-736

[7] Huang W, Jia J, Cummings J, Nelson M, Schneider G, Lindqvist Y., Crystal structure of nitrile hydratase reveals a novel iron centre in a novel fold, 1997, Structure, 5, 691-699

[8] M. Nishiyama et al. Cloning and characterization of genes responsible for metabolism of nitrile compounds from *Pseudomonas chlororaphis* B23, *J. Bacteriol.*, 1991, 173, 2465-2472

[9] Y. Hashimoto et al. Nitrile hydratase gene from *Rhodococcus* sp. N-774 requirement for its downstream region for efficient expression, *Biosci. Biotechnol. Biochem.*, 1994, 58, 1859-1865

[10] K. Liebeton & J. Eck, Identification and expression in *E. coli* of novel nitrile hydratases from the metagenome, *Eng Life Sci.*, 2004, 4, 557-5562

[11] A. W. Bunch, Biotransformation of nitriles by rhodococci, *Antonie Van Leeuwenhoek*, 1998, 74, 89-97

[12] S. Kim & P. Oriel, Cloning and expression of the nitrile hydratase and amidase genes from *Bacillus* sp. BR449 into *Escherichia coli*, *Enzyme Microb Technol.*, 2000, 27, 492-501

[13] L. Martínková & V. Křen, Nitrile- and amide-converting microbial enzymes: stereo-, regio- and chemoselectivity, *Bicat Biotrans*, 2002, 20, 73-93

[14] S. Thomas et al. Biocatalysis: Applications and potentials for the chemical industry, *Trends Biotechnol.*, 2002, 20, 238-242

[15] R. N. Brogden et al. Naproxen up to date: a review of its pharmacological properties and therapeutic efficacy and use in rheumatic diseases and pain states. 1979, Drugs, 18, 241-277

[16] D. L. Anton et al. Process for the preparation of enantiomeric 2-alkanoic acid amides from nitriles, 1997, U.S. Pat. No. 5,593,871

[17] C. S Chen et al. Quantitative analyses of the biochemical kinetic resolutions of enantiomers, 1987, J. Am. Chem. Soc., 104, 7294-7299

[18] C. S Chen, S. Wu, G. Girdaukas, C. J. Sih., Quantitative analyses of the biochemical kinetic resolutions of enantiomers 2: Enzyme catalysed esterification in water-organic solvents biphasic systems, 1987, J. Am. Chem. Soc., 109, 2812-2817

[19] W. R. Pearson and D. J. Lipman, Improved Tools for Biological Sequence Comparison, 1988, Proc. Natl. Acad. Sci., USA 85; 2444-2448

[20] C. Kanz, P. Aldebert, N. Althorpe, W. Baker, A. Baldwin, K. Bates, P. Browne, Al. van den Broek, M. Castro, G. Cochrane, K. Duggan, R. Eberhardt, N. Faruque, J. Gamble, F. G. Diez, N. Harte, T. Kulikova, Q. Lin, V. Lombard, R. Lopez, R. Mancuso, M. McHale, F. Nardone, V. Silventoinen, S. Sobhany, P. Stoehr, M. A. Tuli, K. Tzouvara, R. Vaughan, D. Wu, W. Zhu and R. Apweiler, The EMBL Nucleotide Sequence Database, 2005, Nucleic Acids Res. 33, D29-D33

[21] D. A. Benson, I. K. Mizrachi, D. J. Lipman, J. Ostell, D. L. Wheeler, GenBank, 2005, Nucleic Acids Res. 33, D34-D38

[22] R. Bauer, H. J. Knackmuss & A. Stolz, Enantioselective hydration of 2-arylpropionitriles by a nitrile hydratase from *Agrobacterium tumefaciens* d3, 1998, Appl Microbiol Biotechnol, 49, 89-95

[23] Y. Hashimoto et al., Site-directed mutagenesis for cysteine residues of cobalt-containing nitrile hydratase, J. Inorg Biochem, 2002, 91, 70-77

[24] Minyanaga et al., Mutational and structural analysis of cobalt-containing nitrile hydratase on substrate and metal binding, Eur. J. Biochem, 2004, 271, 429-438

[25] Piersma et al., Arginine 56 mutation in the beta subunit of nitrile hydratase: importance of hydrogen bonding to the non-heme iron center, J Inorg Biochem., 2000, 80, 283-288

[26] Endo et al. Fe-type nitrile hydratses, J Inorg Biochem, 2001, 83, 247-253

[27] Nojiri et al., Cobalt-substituted Fe-type nitrile hydratase of *Rhodococcus* sp. N-771, 2000, FEBS Letters, 465, 173-177

[28] M. Hensel et al., Stereoselective hydration of (RS)-phenylglycine nitrile by new whole cell biocatalysts., 2002, Tetrahedron Asym. 13, 2629-2633.

[29] D. Barettino et al., Improved method for PCR-site directed mutagensis, 1994, Nucleic Acids Res, 22, 541-542

[30] A. Urban et al. A rapid and efficient method for site-directed mutagenesis using one-step overlap extension PCR, 1997, Nucleic Acids Res, 25, 2227-2228

[31] A. Seyfang & J. H. Jin, Multiple site-directed mutagenesis of more than 10 sites simultaneously and in a single round, 2004, Anal Biochem, 324, 285-291

[32] Wieser, M., Takeuchi, K., Wada, Y., Yamada, H. and Nagasawa, T. Low-molecular-mass nitrile hydratase from *Rhodococcus rhodochrous* J1: purification, substrate specificity and comparison with the analogous high-molecular-mass enzyme. 1998, FEMS Microbiol. Lett., 169, 17-22

[33] S. Wu, R. D. Fallon, M. S. Payne, Engineering *Pichia pastoris* for stereoselective nitrile hydrolysis by co-producing three heterologous proteins, 1999, Appl Microbiol Biotechnol, 52, 186-190

[34] M. S. Payne, S. Wu, R. D. Fallon, G. Tudor, B. Stieglitz, J. M. Turner, M. J. Nelson, A stereoselective cobalt-containing nitrile hydratase, 1997, Biochemistry, 36, 5447-5454

[35] A. Stolz, S. Trott, M. Binder, R. Bauer, B. Hirrlinger, N. Layh, & H. J. Knackmuss, Enantioselective hydratases and amidases from different bacterial isolates, 1998, J Mol Cat B, 5, 137-141

[36] A. J. Blakey, mJ. Colby, E. Willams, & C. O'Reilly, Regio- and stereo-specific nitrile hydrolysis by the nitrile hydratase from *Rhodococcus* AJ270, 1995, FEMS Microbiol Letters, 129, 57-62

[37] K. Tamura, Method of producing optically active alpha-hydroxy acid or alpha-hydroxyamide, 2000, EP 0 711 836

[38] R. D. Fallon, B. Stieglitz & I. Turner, A *Pseudomonas putida* capable of stereoselective hydrolysis of nitriles, 1997, Appl Microbiol Biotechnol, 47, 156-161

[39] R. Bauer, Untersuchungen zur Substratspezifität und Enantioselektivität der Nitril-Hydratase aund Amidase aus *Agrobacterium tumefaciens* d3, 1997, PhD-thesis, Stuttgart, Germany

[40] I. Přepechalová, L. Martinková, A. Stolz, M. Ovesná, K. Bezouška, J. Kopecky, V. Křen, Purification abd characterization of the enantioselective nitrile hydratase from *Rhodococcus equi* A4, 2001, Appl Microbiol Biotechnol, 55, 150-156

[41] A. J. J Staathoff & J. A. Jongejan, The enantiomeric ratio: origin, determination and prediction, 1997, Enzyme and Microbial Technology, 21, 559-571.
[42] Pooru et al. JP 1994303971-A/2
[43] Larimer F W, Chain P, Hauser L, Lamerdin J, Malfatti S, Do L, Land M L, Pelletier D A, Beatty J T, Lang A S, Tabita F R, Gibson J L, Hanson T E, Bobst C, Torres J L, Peres C, Harrison F H, Gibson J, Harwood C S., Complete genome sequence of the metabolically versatile photosynthetic bacterium *Rhodopseudomonas palustris*, 2004, *Nature Biotechnol*, 22, 55-61
[44] Fallon et al. U.S. Pat. No. 6,133,411-A/16
[45] Petrillo et al. Appl. Microbiol. Biotechnol. 67(5):664-670 (2005)
[46] Verseck et al. WO2005090595-A/65
[47] Capela D, Barloy-Hubler F, Gouzy J, Bothe G, Ampe F, Batut J, Boistard P, Becker A, Boutry M, Cadieu E, Dreano S, Gloux S, Godrie T, Goffeau A, Kahn D, Kiss E, Lelaure V, Masuy D, Pohl T, Portetelle D, Puhler A, Purnelle B, Ramsperger U, Renard C, Thebault P, Vandenbol M, Weidner S, Galibert F, Analysis of the chromosome sequence of the legume symbiont *Sinorhizobium meliloti* strain 1021, 2001, PNAS, 98, 9877-9882
[48] Mayaux J F, Cerbelaud E, Soubrier F, Yeh P, Blanche F, Petre D., Purification, cloning, and primary structure of a new enantiomer-selective amidase from a *Rhodococcus* strain: structural evidence for a conserved genetic coupling with nitrile hydratase, 1991, *J. Bacteriol.*, 173, 6694-704.
[49] Beppu et al. JP 1992211379-A/2
[50] Osswald et al. WO 2005093080-A 24
[51] Nagsawa et al, WO02070717 A/16
[52] Kiyoshi et al. JP1999253168-A/1
[53] Oikawa et al. WO 2004056990-A/96
[54] Fallon et al. U.S. Pat. No. 6,251,650-A/16

The invention claimed is:

1. An isolated polynucleotide or a pair of isolated polynucleotides encoding an enzyme having nitrile hydratase (NHase) [E.C. 4.2.1.84] activity, wherein the coding sequence is selected from the group consisting of
   (a) a polynucleotide or a pair of polynucleotides having or comprising a nucleotide sequence encoding the α-subunit of the NHase having the amino acid sequence of one of SEQ ID NOs:2, and 6, and the β-subunit of the NHase having the amino acid sequence of one of SEQ ID NOs: 4, and 8;
   (b) a polynucleotide or a pair of polynucleotides having or comprising the nucleotide sequence of one of SEQ ID NOs:1, and 5 and encoding the α-subunit of the NHase, and the nucleotide sequence of one of SEQ ID NOs:3, and 7, encoding the β-subunit of the NHase;
   (c) a polynucleotide or a pair of polynucleotides comprising a nucleotide sequence which is at least 97% identical to the polynucleotide encoding the β-subunit of the NHase of one of SEQ ID NOs:3, or 7, or at least 97% identical to the polynucleotide encoding the α-subunit of the NHase of one of SEQ ID NOs:1, or 5; and
   (d) a polynucleotide or a pair of polynucleotides having a nucleotide sequence being degenerate as a result of the genetic code to the polynucleotide or pair of polynucleotides of (c); or the 100% complementary strand or pair of 100% complementary strands of such a polynucleotide or pair of polynucleotides of (a) to (c).

2. The polynucleotide or a pair of polynucleotides of claim 1, wherein said polynucleotide or a pair of polynucleotides is selected from:
   (a) a polynucleotide or a pair of polynucleotides having or comprising a nucleotide sequence encoding pairs of α- and β-subunits of the NHase, wherein the pairs of subunits have the amino acid sequences: (i) SEQ ID NOs: 2 and 4, or (ii) SEQ ID NOs:6 and 8;
   (b) a polynucleotide or a pair of polynucleotides polynucleotide having or comprising a nucleotide sequence encoding pairs of α- and β-subunits of the NHase, wherein the pairs of nucleotide sequences are: (i) SEQ ID NOs: 1 and 3, or (ii) SEQ ID NOs: 5 and 7;
   (c) a polynucleotide or a pair of polynucleotides comprising a nucleotide sequence which is at least 97% identical to the polynucleotide encoding the β-subunit of the NHase of one of SEQ ID NOs:3, or 7, or at least 97% identical to the polynucleotide encoding the α-subunit of the NHase of one of SEQ ID NOs:1, or 5 and wherein the polynucleotide or pair of polynucleotides have a nucleotide sequence encoding a pair of an α- and a β-subunit having the required identity with the pairs of nucleotide sequences of (i) SEQ ID NOs:1 and 3, or (ii) SEQ ID NOs:5 and 7; and
   (d) a polynucleotide or a pair of polynucleotides having or comprising a nucleotide sequence being degenerate as a result of the genetic code to the nucleotide sequence of the polynucleotide or pair of polynucleotides of (c); or the 100% complementary strand or pair of 100% complementary strands of such a polynucleotide or pair of polynucleotides of (a) to (c).

3. The polynucleotide or a pair of polynucleotides according to claim 1, wherein at least one of the coding regions for the α- or the β-subunit is fused with a heterologous or homologous polynucleotide.

4. The polynucleotide of claim 3, wherein said heterologous or homologous polynucleotide encodes a polypeptide.

5. A vector containing the polynucleotide of claim 1.

6. A host genetically engineered with the polynucleotide of claim 1.

7. A process for producing a pair of polypeptides, forming a heteromultimer, or a fusion protein having nitrile hydratase (NHase) [E.C. 4.2.1.84] activity and consisting of or comprising (an) α- and (a) β-subunit(s), the process comprising culturing the host of claim 6 and recovering the pair of polypeptides or fusion protein encoded by said polynucleotide or pair of polynucleotides.

8. A process for producing bacteria or eukaryotic cells capable of expressing a pair of polypeptides or a fusion protein having nitrile hydratase (NHase) [E.C. 4.2.1.84] activity and consisting of or comprising (an) α- and (a) β-subunit(s), the process comprising genetically engineering bacteria or eukaryotic cells with the vector of claim 5.

9. A composition comprising the polynucleotide or pair of polynucleotides of claim 1.

10. An isolated polynucleotide or a pair of isolated polynucleotides encoding an enzyme having nitrile hydratase (NHase) [E.C. 4.2.1.84] activity, wherein the coding sequence is selected from the group consisting of:
    (a) a polynucleotide or a pair of polynucleotides having or comprising a nucleotide sequence encoding an α-subunit and a β-subunit of the NHase, wherein
       (i) the α-subunit has the amino acid sequence of one of SEQ ID NOs:2, or 6; or
       (ii) the β-subunit of the NHase has the amino acid sequence of one of SEQ ID NOs:4, or 8;
    (b) a polynucleotide or a pair of polynucleotides having or comprising a nucleotide sequence encoding an α-subunit and a β-subunit of the NHase, wherein
       (i) the α-subunit has the nucleotide sequence of one of SEQ ID NOs:1, or 5 and encoding an α-subunit of the NHase; or
       (ii) the β-subunit has the nucleotide sequence of one of SEQ ID NOs:3, or 7 and encoding a β-subunit of the NHase;
    (c) a polynucleotide or a pair of polynucleotides comprising a nucleotide sequence encoding an α-subunit and a β-subunit of the NHase, wherein
       (i) the nucleotide sequence encoding the α-subunit of the NHase is at least 97% identical to a nucleotide sequence of one of SEQ ID NOs:1, or 5; or
       (ii) the nucleotide sequence encoding the β-subunit of the NHase is at least 97% identical to a nucleotide sequence of one of SEQ ID NOs:3, or;

(d) a polynucleotide or a pair of polynucleotides having or comprising a nucleotide sequence being degenerate as a result of the genetic code to the nucleotide sequence of the polynucleotide or pair of polynucleotides of (d) or (c); or the 100% complementary strand or pair of 100% complementary strands of such a polynucleotide or pair of polynucleotides of (a) to (c) or fragments thereof useful as specific probes or primers.

\* \* \* \* \*

SEQUENCE LISTING

```
<160> NUMBER OF SEQ ID NOS: 29

<210> SEQ ID NO 1
<211> LENGTH: 609
<212> TYPE: DNA
<213> ORGANISM: Raoultella terrigena, strain 77.1

<400> SEQUENCE: 1
atgagccata aacacgacca cgaccacacc gaaccaccag tagacatcga gttacgtgtc      60
cgcgcactgg aatccctgct acaggaaaaa ggactaatcg acccggcggc tctggatgag     120
ttgattgaca cctatgagca caaagtcggc ccgcgcaatg gcgcacaggt tgtcgccaga     180
gcgtggagcg acccggaata caaacgtcga ctgatggaaa acgccaccgc cgccatctca     240
gaactgggtt tctccggtat acagggcgaa gacatgttgg tggttgagaa cacgccggac     300
gtgcacaacg tcaccgtctg cacgctgtgc tcctgctacc cctggccggt actgggtctg     360
ccacctgtct ggtacaaatc agcccccctat cgttcgcgta ttgtcatcga cccacgcggc     420
gttctggccg agttcgggtt acacattccc gaaagcaaag agattcgcgt ctgggacagc     480
agcgccgagt tgcgttatct ggtactgcct gaacgtccgg cgggcacaga cggctggagc     540
gaagcgcagt tgagcgaact gatctcgcgc gattcgatga ttggcaccgg tgtggttacc     600
gcaccataa                                                             609

<210> SEQ ID NO 2
<211> LENGTH: 202
<212> TYPE: PRT
<213> ORGANISM: Raoultella terrigena, strain 77.1

<400> SEQUENCE: 2

Met Ser His Lys His Asp His Asp His Thr Glu Pro Pro Val Asp Ile
1               5                   10                  15

Glu Leu Arg Val Arg Ala Leu Glu Ser Leu Leu Gln Glu Lys Gly Leu
            20                  25                  30

Ile Asp Pro Ala Ala Leu Asp Glu Leu Ile Asp Thr Tyr Glu His Lys
        35                  40                  45

Val Gly Pro Arg Asn Gly Ala Gln Val Val Ala Arg Ala Trp Ser Asp
    50                  55                  60

Pro Glu Tyr Lys Arg Arg Leu Met Glu Asn Ala Thr Ala Ala Ile Ser
65                  70                  75                  80

Glu Leu Gly Phe Ser Gly Ile Gln Gly Glu Asp Met Leu Val Val Glu
```

```
                    85                  90                  95
Asn Thr Pro Asp Val His Asn Val Thr Val Cys Thr Leu Cys Ser Cys
            100                 105                 110

Tyr Pro Trp Pro Val Leu Gly Leu Pro Pro Val Trp Tyr Lys Ser Ala
            115                 120                 125

Pro Tyr Arg Ser Arg Ile Val Ile Asp Pro Arg Gly Val Leu Ala Glu
            130                 135                 140

Phe Gly Leu His Ile Pro Glu Ser Lys Glu Ile Arg Val Trp Asp Ser
145                 150                 155                 160

Ser Ala Glu Leu Arg Tyr Leu Val Leu Pro Glu Arg Pro Ala Gly Thr
                    165                 170                 175

Asp Gly Trp Ser Glu Ala Gln Leu Ser Glu Leu Ile Ser Arg Asp Ser
            180                 185                 190

Met Ile Gly Thr Gly Val Val Thr Ala Pro
            195                 200

<210> SEQ ID NO 3
<211> LENGTH: 654
<212> TYPE: DNA
<213> ORGANISM: Raoultella terrigena, strain 77.1

<400> SEQUENCE: 3
atgaacggga tacacgatct cggcggtatg cacggcttcg gcccgatccc taccgaggaa      60
aacgagccct atttccacca tgagtgggag cgccgggtct ttccaatgtt cgcctcgttg     120
tttgtcggcg tacactttaa cgtcgacgaa tttcgccatt ccatcgaatg tatgccccct     180
gccgactatc tgcagtcgag ttactacgag cactggctgc atgcattcga aaccctgctg     240
ctggcaaagg gggtgatcac cgttgacgag ttgtggggtg cgcgaagcc caccctctgt     300 aagccaggca cacctgtgct gacgcaggac atggtatcga tggtcgtcag caccggcggc     360
tctgctcgcg tcagtcacga cgttgcgccc cgcttccggg tgggagatcg ggtacgaacg     420
aaaaatttca acccgaccac ccatacccgt ctgccgcgtt acgcacgcga taaagtcggc     480
cgcatagaaa ttgctcacgg tgtgtttatc acgccagata ccgcggcgca tggcctgggc     540
gaacatcccc agcatgtcta cagcgtcagt ttcaccgcgc aggagctgtg ggggggaacca     600 cgcccggaca cgtgttcat cgatctgtgg gacgactatc tggaggaagc atga           654

<210> SEQ ID NO 4
<211> LENGTH: 217
<212> TYPE: PRT
<213> ORGANISM: Raoultella terrigena, strain 77.1

<400> SEQUENCE: 4

Met Asn Gly Ile His Asp Leu Gly Gly Met His Gly Phe Gly Pro Ile
1               5                   10                  15

Pro Thr Glu Glu Asn Glu Pro Tyr Phe His His Glu Trp Glu Arg Arg
            20                  25                  30

Val Phe Pro Met Phe Ala Ser Leu Phe Val Gly Val His Phe Asn Val
        35                  40                  45

Asp Glu Phe Arg His Ser Ile Glu Cys Met Pro Pro Ala Asp Tyr Leu
    50                  55                  60

Gln Ser Ser Tyr Tyr Glu His Trp Leu His Ala Phe Glu Thr Leu Leu
65                  70                  75                  80

Leu Ala Lys Gly Val Ile Thr Val Asp Glu Leu Trp Gly Gly Ala Lys
                    85                  90                  95

Pro Thr Leu Cys Lys Pro Gly Thr Pro Val Leu Thr Gln Asp Met Val
```

```
                    100                 105                 110
Ser Met Val Val Ser Thr Gly Gly Ser Ala Arg Val Ser His Asp Val
            115                 120                 125

Ala Pro Arg Phe Arg Val Gly Asp Arg Val Arg Thr Lys Asn Phe Asn
        130                 135                 140

Pro Thr Thr His Thr Arg Leu Pro Arg Tyr Ala Arg Asp Lys Val Gly
145                 150                 155                 160

Arg Ile Glu Ile Ala His Gly Val Phe Ile Thr Pro Thr Ala Ala
                165                 170                 175

His Gly Leu Gly Glu His Pro Gln His Val Tyr Ser Val Ser Phe Thr
                180                 185                 190

Ala Gln Glu Leu Trp Gly Glu Pro Arg Pro Asp Asn Val Phe Ile Asp
        195                 200                 205

Leu Trp Asp Asp Tyr Leu Glu Glu Ala
        210                 215
```

<210> SEQ ID NO 5
<211> LENGTH: 609
<212> TYPE: DNA
<213> ORGANISM: Raoultella terrigena, strain 37.1

<400> SEQUENCE: 5

```
atgagccata aacacgacca cgaccacacc gaaccaccaa tagacatcga gttacgtgtc      60
cgcgcactgg aatccctgct acaggaaaaa ggactaatcg accctgcggc tctggatgag     120
ttgattgaca cctatgagca caaagtcggc ccgcgcaatg cgcacaggt tgtcgccaga      180
gcgtggagcg acccggaata caaacgtcga ctgatggaaa acgccaccgc cgccatctca     240
gaactgggtt tctccggtat acagggcgaa gacatgttgg tggttgagaa tacgccggac     300
gtgcacaacg tgaccgtctg tacgctgtgc tcctgctacc cctggccggt actgggtctg     360
ccacctgtct ggtacaaatc agcaccctat cgttcgcgta ttgtcatcga cccacgcggc     420
gttctggccg agttcgggtt acacattccc gaaagcaaag agattcgcgt ctgggacagc     480
agcgccgagt tgcgttatct ggtactgcct gaacgtccgg cgggtacaga cggctggagc     540
gaagcgcagt tgagcgaact gatctcgcgc gattcgatga ttggcaccgg tgtggttacc     600
gcaccataa                                                            609
```

<210> SEQ ID NO 6
<211> LENGTH: 202
<212> TYPE: PRT
<213> ORGANISM: Raoultella terrigena, strain 37.1

<400> SEQUENCE: 6

```
Met Ser His Lys His Asp His Asp His Thr Glu Pro Pro Ile Asp Ile
1               5                   10                  15

Glu Leu Arg Val Arg Ala Leu Glu Ser Leu Leu Gln Glu Lys Gly Leu
            20                  25                  30

Ile Asp Pro Ala Ala Leu Asp Glu Leu Ile Asp Thr Tyr Glu His Lys
        35                  40                  45

Val Gly Pro Arg Asn Gly Ala Gln Val Val Ala Arg Ala Trp Ser Asp
    50                  55                  60

Pro Glu Tyr Lys Arg Arg Leu Met Glu Asn Ala Thr Ala Ala Ile Ser
65                  70                  75                  80

Glu Leu Gly Phe Ser Gly Ile Gln Gly Glu Asp Met Leu Val Val Glu
                85                  90                  95

Asn Thr Pro Asp Val His Asn Val Thr Val Cys Thr Leu Cys Ser Cys
```

```
                    100                 105                 110
Tyr Pro Trp Pro Val Leu Gly Leu Pro Pro Val Trp Tyr Lys Ser Ala
            115                 120                 125

Pro Tyr Arg Ser Arg Ile Val Ile Asp Pro Arg Gly Val Leu Ala Glu
        130                 135                 140

Phe Gly Leu His Ile Pro Glu Ser Lys Glu Ile Arg Val Trp Asp Ser
145                 150                 155                 160

Ser Ala Glu Leu Arg Tyr Leu Val Leu Pro Glu Arg Pro Ala Gly Thr
                165                 170                 175

Asp Gly Trp Ser Glu Ala Gln Leu Ser Glu Leu Ile Ser Arg Asp Ser
            180                 185                 190

Met Ile Gly Thr Gly Val Val Thr Ala Pro
            195                 200

<210> SEQ ID NO 7
<211> LENGTH: 654
<212> TYPE: DNA
<213> ORGANISM: Raoultella terrigena, strain 37.1

<400> SEQUENCE: 7
atgaacggga tacacgatct cggcggtatg cacggcttcg gcccgatccc taccgaggaa      60
aatgagccct atttccacca tgagtgggag cgccgggtat ttccaatgtt cgcctcgttg     120
tttgtcggcg gacacttcaa cgtcgacgaa tttcgccatt ccatcgaatg tatgcctcct     180
gccgactatc tgcagtcgag ttactacgag cactggctgc atgcattcga aaccctgctg     240
ctggcaaagg gggtgatcac cgttgacgag ttgtggggtg gcgcgaagcc tacccttcgt     300
aagcctggca cacctgtgct gacgcaggac atggtatcga tggtcgtcag caccggcggc     360
tctgctcgcg tcagtcacga cgttgcgccc cgcttccggg tgggagatcg ggtacgaacg     420
aaaaatttca acccgaccac ccatacccgt ctgccccgtt acgcacgcga taaagtcggc     480
cgcatagaaa ttgctcacgg tgtgtttatc acgccagata ccgcgcgca cggcctgggc      540 gaacatcccc agcatgtcta cagcgtcagt ttcaccgcgc aggagctgtg ggggaaccca     600
cgcccggaca acgtgttcat cgatctgtgg gacgactatc tggaggaagc atga          654

<210> SEQ ID NO 8
<211> LENGTH: 217
<212> TYPE: PRT
<213> ORGANISM: Raoultella terrigena, strain 37.1

<400> SEQUENCE: 8

Met Asn Gly Ile His Asp Leu Gly Gly Met His Gly Phe Gly Pro Ile
1               5                   10                  15

Pro Thr Glu Glu Asn Glu Pro Tyr Phe His His Glu Trp Glu Arg Arg
            20                  25                  30

Val Phe Pro Met Phe Ala Ser Leu Phe Val Gly Gly His Phe Asn Val
        35                  40                  45

Asp Glu Phe Arg His Ser Ile Glu Cys Met Pro Pro Ala Asp Tyr Leu
    50                  55                  60

Gln Ser Ser Tyr Tyr Glu His Trp Leu His Ala Phe Glu Thr Leu Leu
65                  70                  75                  80

Leu Ala Lys Gly Val Ile Thr Val Asp Glu Leu Trp Gly Gly Ala Lys
                85                  90                  95

Pro Thr Leu Cys Lys Pro Gly Thr Pro Val Leu Thr Gln Asp Met Val
            100                 105                 110

Ser Met Val Val Ser Thr Gly Gly Ser Ala Arg Val Ser His Asp Val
```

```
             115                 120                 125
Ala Pro Arg Phe Arg Val Gly Asp Arg Val Arg Thr Lys Asn Phe Asn
        130                 135                 140

Pro Thr Thr His Thr Arg Leu Pro Arg Tyr Ala Arg Asp Lys Val Gly
145                 150                 155                 160

Arg Ile Glu Ile Ala His Gly Val Phe Ile Thr Pro Asp Thr Ala Ala
                165                 170                 175

His Gly Leu Gly Glu His Pro Gln His Val Tyr Ser Val Ser Phe Thr
            180                 185                 190

Ala Gln Glu Leu Trp Gly Glu Pro Arg Pro Asp Asn Val Phe Ile Asp
        195                 200                 205

Leu Trp Asp Asp Tyr Leu Glu Glu Ala
    210                 215
```

<210> SEQ ID NO 9
<211> LENGTH: 663
<212> TYPE: DNA
<213> ORGANISM: Pantoea sp., strain 17.3.1

<400> SEQUENCE: 9

```
atgaacggta tacacgattg tggaggaatg cagaatctcg gcgctattcc tctggaagag        60
aacgaaccgg tttttcatgc cgaatgggaa aaagcgattt tggtgatgac cattaacggt       120
tttctcagcg ggagcatcct ggtggacaac ttcaggcacc aaattgaaaa aatgccagcc       180
agcgaatatc tgctcacctc ctattacgaa cactgggttt ttgccatgga acatctactc       240
atcaataaca acacgattac ccgtgaagca ttggaatcca gaatggctga actggcagag       300
agagttgaaa tgagcgcgat agctaaagag accttcctgg agttgattaa aaccacgcca       360
aactaccatc gtgaaagtga tcgatagcg cggtttgcgc caggcgatac cattcgtacc       420
tgcgaactga acacgccggg tcatacgcgt ttgccgcgtt atgcacgcga taagacagga       480
gtaattatcg ccatgtatgg cgtgtgtgtt tttccggact cactgacgcg tgacggaagt       540
gaagacccgc agcacgttta tctggtgcag ttctcgtcag ccgatctttg ggggctggc        600 tcagaaccat ttactgtcag cttgagcctg ttcgaaagtt atattgctga aaagtggag        660 taa                                                                      663
```

<210> SEQ ID NO 10
<211> LENGTH: 194
<212> TYPE: PRT
<213> ORGANISM: Pantoea sp., strain 17.3.1

<400> SEQUENCE: 10

```
Met Ser Asn His Asp Val Leu Pro Ser Glu Ser Ala Leu Lys Val Arg
1               5                   10                  15

Ala Ile Gln Ser Leu Leu Thr Glu Lys Gly Leu Leu Asp Pro Gln Thr
            20                  25                  30

Ser Asp Ala Ile Val Asp Tyr Phe Glu Asn Lys Ile Gly Pro Arg Asn
        35                  40                  45

Gly Ala Ser Val Val Ala Arg Ala Trp Leu Asp Ala Glu Phe Lys Lys
    50                  55                  60

Lys Leu Leu Glu Asp Gly Thr Thr Ala Ile Ser Glu Met Gly Phe Ser
65                  70                  75                  80

Gly Ala Glu Gly Ala Val Ile His Val Leu Glu Asn Thr Asp Ala Val
                85                  90                  95

His Asn Ile Val Val Cys Thr Leu Cys Ser Cys Tyr Pro Trp Pro Val
            100                 105                 110
```

```
Leu Gly Leu Pro Pro Ile Trp Phe Lys Ser Ala Gln Tyr Arg Ser Arg
            115                 120                 125

Val Val Ile Asp Pro Arg Gly Val Leu Lys Glu Phe Gly Thr Glu Leu
        130                 135                 140

Pro Pro Glu Lys Glu Ile Arg Val Trp Asp Ser Asn Ala Glu Ile Arg
145                 150                 155                 160

Tyr Phe Val Leu Pro Gln Arg Pro Ala Gly Thr Glu Asn Leu Ser Glu
                165                 170                 175

Glu Gln Leu Ala Ala Arg Val Thr Arg Asp Ser Met Ile Gly Thr Gly
            180                 185                 190

Ile Leu

<210> SEQ ID NO 11
<211> LENGTH: 585
<212> TYPE: DNA
<213> ORGANISM: Pantoea sp., strain 17.3.1

<400> SEQUENCE: 11
atgtcaaatc atgatgtctt accttccgaa agtgccctca agtgcgggc gattcagtca      60 ctcctgacgg agaaaggttt gctcgatcca caaacttcag acgccatcgt ggactatttt     120
gaaaacaaaa tcggtccccg caacggtgca agtgtcgtgg cgcgtgcctg cttgatgcc     180 gaattcaaaa agaagctgct tgaagatggc actactgcca tcagcgagat ggggttctca     240
ggtgccgaag cgcagtcat tcacgtgctc gaaaacactg atgcggtgca taacatcgtc     300
gtttgtacgc tgtgctcctg ttatccgtgg ccggtactgg ggttaccgcc aatctggttt     360
aagtctgcac agtaccgctc ccgtgtggtg attgatccaa gaggcgtgct gaaggagttc     420
ggtactgagc ttccacctga aaagagatt cgcgtatggg acagcaatgc cgaaatccgc     480
tatttcgtat tgccgcaacg cccggcgggc acggagaacc tgagtgaaga caactggcc     540 gcgagagtga cccgcgattc aatgattggt acgggcatcc tttaa                    585

<210> SEQ ID NO 12
<211> LENGTH: 220
<212> TYPE: PRT
<213> ORGANISM: Pantoea sp., strain 17.3.1

<400> SEQUENCE: 12

Met Asn Gly Ile His Asp Cys Gly Gly Met Gln Asn Leu Gly Ala Ile
1               5                   10                  15

Pro Leu Glu Glu Asn Glu Pro Val Phe His Ala Glu Trp Glu Lys Ala
            20                  25                  30

Ile Leu Val Met Thr Ile Asn Gly Phe Leu Ser Gly Ser Ile Leu Val
        35                  40                  45

Asp Asn Phe Arg His Gln Ile Glu Lys Met Pro Ala Ser Glu Tyr Leu
    50                  55                  60

Leu Thr Ser Tyr Tyr Glu His Trp Val Phe Ala Met Glu His Leu Leu
65                  70                  75                  80

Ile Asn Asn Asn Thr Ile Thr Arg Glu Ala Leu Glu Ser Arg Met Ala
                85                  90                  95

Glu Leu Ala Glu Arg Val Glu Met Ser Ala Ile Ala Lys Glu Thr Phe
            100                 105                 110

Leu Glu Leu Ile Lys Thr Thr Pro Asn Tyr His Arg Glu Ser Asp Ala
        115                 120                 125

Ile Ala Arg Phe Ala Pro Gly Asp Thr Ile Arg Thr Cys Glu Leu Asn
    130                 135                 140
```

```
Thr Pro Gly His Thr Arg Leu Pro Arg Tyr Ala Arg Asp Lys Thr Gly
145                 150                 155                 160

Val Ile Ile Ala Met Tyr Gly Val Cys Val Phe Pro Asp Ser Leu Thr
                165                 170                 175

Arg Asp Gly Ser Glu Asp Pro Gln His Val Tyr Leu Val Gln Phe Ser
            180                 185                 190

Ser Ala Asp Leu Trp Gly Ala Gly Ser Glu Pro Phe Thr Val Ser Leu
        195                 200                 205

Ser Leu Phe Glu Ser Tyr Ile Ala Glu Lys Val Glu
    210                 215                 220
```

<210> SEQ ID NO 13
<211> LENGTH: 603
<212> TYPE: DNA
<213> ORGANISM: Brevibacterium linens, strain 32B.1

<400> SEQUENCE: 13

```
atgagcgaca agatacgcag ccaagaagag atcgcagctc gggtcaaagc actggaatcg    60
atgctgatcg agaagggcat catgaccact caagccatcg acagactggt ggagatctac   120
gagaacgaag tcggacctca gctcggggcg aaggtcgtcg ccaaggcgtg gtcggatccg   180
ggattcaaat ccagacttct caccgacgca acaggtgcct gcggcgaact cggtatcggc   240
ggcctccagg gtgaagacat ggtcgtcgtg aagacaccg acaccgtcca acgtcatc     300
gtctgcacct tgtgttcgtg ctacccgtgg ccggttctcg gcttccccc gaactggtac   360
aaggacccgc agtaccgggc cgcgatctgc cgcgaacccc gcaaagtcct ctccgaaagc   420
ttcggataca ccgtctccaa tgacgtcgag atccgagtct gggactccag cagcgaaatg   480
cggtactggg tcctgccccg acgcccagac ggaaccgacg gatggaccga agaccaactc   540
gctgatctgg tcagccgcga ctccatgatc ggcgtcggcc ccaccgcgaa ggcgcagtca   600
tga                                                                603
```

<210> SEQ ID NO 14
<211> LENGTH: 200
<212> TYPE: PRT
<213> ORGANISM: Brevibacterium linens, strain 32B.1

<400> SEQUENCE: 14

```
Met Ser Asp Lys Ile Arg Ser Gln Glu Glu Ile Ala Ala Arg Val Lys
1               5                   10                  15

Ala Leu Glu Ser Met Leu Ile Glu Lys Gly Ile Met Thr Thr Gln Ala
            20                  25                  30

Ile Asp Arg Leu Val Glu Ile Tyr Glu Asn Glu Val Gly Pro Gln Leu
        35                  40                  45

Gly Ala Lys Val Val Ala Lys Ala Trp Ser Asp Pro Gly Phe Lys Ser
    50                  55                  60

Arg Leu Leu Thr Asp Ala Thr Gly Ala Cys Gly Glu Leu Gly Ile Gly
65                  70                  75                  80

Gly Leu Gln Gly Glu Asp Met Val Val Val Asp Thr Asp Thr Val
                85                  90                  95

His Asn Val Ile Val Cys Thr Leu Cys Ser Cys Tyr Pro Trp Pro Val
                100                 105                 110

Leu Gly Leu Pro Pro Asn Trp Tyr Lys Asp Pro Gln Tyr Arg Ala Ala
        115                 120                 125

Ile Cys Arg Glu Pro Arg Lys Val Leu Ser Glu Ser Phe Gly Tyr Thr
    130                 135                 140
```

```
Val Ser Asn Asp Val Glu Ile Arg Val Trp Asp Ser Ser Glu Met
145                 150                 155                 160

Arg Tyr Trp Val Leu Pro Arg Arg Pro Asp Gly Thr Asp Gly Trp Thr
                165                 170                 175

Glu Asp Gln Leu Ala Asp Leu Val Ser Arg Asp Ser Met Ile Gly Val
            180                 185                 190

Gly Pro Thr Ala Lys Ala Gln Ser
        195                 200
```

<210> SEQ ID NO 15
<211> LENGTH: 708
<212> TYPE: DNA
<213> ORGANISM: Brevibacterium linens, strain 32B.1

<400> SEQUENCE: 15

```
atgaacggag ttttcgacct ggccgggacc gacggtctgg gtccggtcgt tgtccccgac    60
gacgagccaa tcttccgcgc ggaatgggag aaagccgcgt tcggcatgtt ctcgatgtgc   120
tttcgcggcg gcttttcgg cgtcgaccag tttcggtacg gcatggaaca gatcgacccc   180
gccgtctacc tcaaatcgcc gtactacgag cactggatcc acaccgtcga gtaccacggc   240
gaacgcaccg gtcaactcga cctcgacgaa ctcgaccgca gaaccgagta ctacctggcc   300
aacccggacg caccgatgcc cgaacacgcc gacgacccag aactactagc gttcatcaac   360
gccgtcgttc cagccggtgc accggccaaa gcgaaagcg acaagatcgc cgcttttcaa   420
gtcggcgaca cggtgaaagt tctgcgcgac tcgccccgcg gtcacacccg gcgcgcccgt   480
tacatccgcg gcgcgaccgg tgaaatcgtg ctggcacacg gcacgttcat ctacccagac   540
accgcaggca caacctcgg tgaatgtccg gaacacgtct acaccgtccg ctttacagcc   600
gaagaactct ggggcgcaga gacagccgag cccaaccaat ccgtctactt cgacgtctgg   660
gaccctaca tcgaactcgt cacacccga ggagcacagt cagcatga               708
```

<210> SEQ ID NO 16
<211> LENGTH: 235
<212> TYPE: PRT
<213> ORGANISM: Brevibacterium linens, strain 32B.1

<400> SEQUENCE: 16

```
Met Asn Gly Val Phe Asp Leu Ala Gly Thr Asp Gly Leu Gly Pro Val
1               5                   10                  15

Val Val Pro Asp Asp Glu Pro Ile Phe Arg Ala Glu Trp Glu Lys Ala
            20                  25                  30

Ala Phe Gly Met Phe Ser Met Cys Phe Arg Gly Gly Phe Gly Val
        35                  40                  45

Asp Gln Phe Arg Tyr Gly Met Glu Gln Ile Asp Pro Ala Val Tyr Leu
    50                  55                  60

Lys Ser Pro Tyr Tyr Glu His Trp Ile His Thr Val Glu Tyr His Gly
65                  70                  75                  80

Glu Arg Thr Gly Gln Leu Asp Leu Asp Glu Leu Asp Arg Arg Thr Glu
                85                  90                  95

Tyr Tyr Leu Ala Asn Pro Asp Ala Pro Met Pro Glu His Ala Asp Asp
            100                 105                 110

Pro Glu Leu Leu Ala Phe Ile Asn Ala Val Val Pro Ala Gly Ala Pro
        115                 120                 125

Ala Lys Arg Glu Ser Asp Lys Ile Ala Arg Phe Gln Val Gly Asp Thr
    130                 135                 140
```

```
Val Lys Val Leu Arg Asp Ser Pro Arg Gly His Thr Arg Ala Arg
145                 150                 155                 160

Tyr Ile Arg Gly Ala Thr Gly Glu Ile Val Leu Ala His Gly Thr Phe
            165                 170                 175

Ile Tyr Pro Asp Thr Ala Gly Asn Asn Leu Gly Glu Cys Pro Glu His
            180                 185                 190

Val Tyr Thr Val Arg Phe Thr Ala Glu Glu Leu Trp Gly Ala Glu Thr
            195                 200                 205

Ala Glu Pro Asn Gln Ser Val Tyr Phe Asp Val Trp Asp Pro Tyr Ile
        210                 215                 220

Glu Leu Val Thr Pro Arg Gly Ala Gln Ser Ala
225                 230                 235

<210> SEQ ID NO 17
<211> LENGTH: 609
<212> TYPE: DNA
<213> ORGANISM: Klebsiella oxytoca, strain 38.1.2

<400> SEQUENCE: 17
atgagccata acacgacca cgaccatacc caacccccg ttgatatcga gctacgcgtc      60
cgcgcactgg aatccctgct gcaggaaaaa ggcctgatcg acccggctgc gctggatgag    120
ctgattgaca cctacgagca caagtcggc ccccgaaacg gcgcacaggt tgtcgccaga    180
gcgtggagcg acccggaata caaacgtcga ctgatggaaa acgccactgc cgctattgct    240
gaactgggtt tctccggaat acagggcgaa gacatgctgg tcgtggagaa cacgccggac    300
gtgcacaacg tcaccgtttg tacgctgtgt cctgctacc cctggccggt actgggtctg    360
ccgccggtgt ggtacaaatc agcgcccta cgttcgcgta tcgtcatcga cccgcgcggc    420
gttctcgccg agttcgggtt acacatacca gaaaacaaag agattcgcgt ctgggatagc    480
agcgccgagc tgcgctatct ggtcctgcct gaacgtccgg caggcacgga aggctggagc    540
gaagcgcagt tgagcgaact catcacgcgc gattcgatga ttggcaccgg tgtggttacc    600
gcaccataa                                                           609

<210> SEQ ID NO 18
<211> LENGTH: 202
<212> TYPE: PRT
<213> ORGANISM: Klebsiella oxytoca, strain 38.1.2

<400> SEQUENCE: 18

Met Ser His Lys His Asp His Asp His Thr Gln Pro Pro Val Asp Ile
1               5                   10                  15

Glu Leu Arg Val Arg Ala Leu Glu Ser Leu Leu Gln Glu Lys Gly Leu
            20                  25                  30

Ile Asp Pro Ala Ala Leu Asp Glu Leu Ile Asp Thr Tyr Glu His Lys
        35                  40                  45

Val Gly Pro Arg Asn Gly Ala Gln Val Val Ala Arg Ala Trp Ser Asp
    50                  55                  60

Pro Glu Tyr Lys Arg Arg Leu Met Glu Asn Ala Thr Ala Ala Ile Ala
65                  70                  75                  80

Glu Leu Gly Phe Ser Gly Ile Gln Gly Glu Asp Met Leu Val Val Glu
                85                  90                  95

Asn Thr Pro Asp Val His Asn Val Thr Val Cys Thr Leu Cys Ser Cys
            100                 105                 110

Tyr Pro Trp Pro Val Leu Gly Leu Pro Pro Val Trp Tyr Lys Ser Ala
        115                 120                 125
```

-continued

Pro Tyr Arg Ser Arg Ile Val Ile Asp Pro Arg Gly Val Leu Ala Glu
              130                 135                 140

Phe Gly Leu His Ile Pro Glu Asn Lys Glu Ile Arg Val Trp Asp Ser
145                 150                 155                 160

Ser Ala Glu Leu Arg Tyr Leu Val Leu Pro Glu Arg Pro Ala Gly Thr
                165                 170                 175

Glu Gly Trp Ser Glu Ala Gln Leu Ser Glu Leu Ile Thr Arg Asp Ser
            180                 185                 190

Met Ile Gly Thr Gly Val Val Thr Ala Pro
            195                 200

<210> SEQ ID NO 19
<211> LENGTH: 654
<212> TYPE: DNA
<213> ORGANISM: Klebsiella oxytoca , strain 38.1.2

<400> SEQUENCE: 19
atgaacggga tacacgatct ggggggatg cacggccttg gcccgatccc taccgaggaa      60
aacgagccct atttccatca tgagtgggaa cgccgggtat ttcctctgtt cgcctcgttg    120
ttcgtcggcg gacactttaa cgtcgatgaa tttcgccacg ccatcgaacg tatggcgccg    180
accgaatatc tgcagtcgag ctactacgag cactggctgc atgcattcga aacgctgctg    240
ctggcaaagg gggtgatcac cgttgaagaa ctgtggggtg gcgcgaagcc tgccccctgc    300
aagcctggca cacctgtgct gacgcaggag atggtgtcga tggtggtcag caccggcggg    360
tctgctcggg tcagtcacga tgttgcgccc gcttccggg tgggcgattg ggtacgaacg     420
aaaaatttca acccgaccac ccatacccgc ctgccacgct acgacgcga taaagtcggt     480 cgcatagaga tcgctcacgg tgtgtttatc acgccagata ctgcggcgca cgggctgggc    540
gaacatcccc aacatgttta cagcgtcagt ttcaccgcgc aggcgctatg gggagagccg    600
cgccctgaca agtgttcat cgatctgtgg gacgactatc tggaggaagc ataa           654

<210> SEQ ID NO 20
<211> LENGTH: 217
<212> TYPE: PRT
<213> ORGANISM: Klebsiella oxytoca, strain 38.1.2

<400> SEQUENCE: 20

Met Asn Gly Ile His Asp Leu Gly Gly Met His Gly Leu Gly Pro Ile
1               5                   10                  15

Pro Thr Glu Glu Asn Glu Pro Tyr Phe His His Glu Trp Glu Arg Arg
            20                  25                  30

Val Phe Pro Leu Phe Ala Ser Leu Phe Val Gly Gly His Phe Asn Val
        35                  40                  45

Asp Glu Phe Arg His Ala Ile Glu Arg Met Ala Pro Thr Glu Tyr Leu
    50                  55                  60

Gln Ser Ser Tyr Tyr Glu His Trp Leu His Ala Phe Glu Thr Leu Leu
65                  70                  75                  80

Leu Ala Lys Gly Val Ile Thr Val Glu Glu Leu Trp Gly Gly Ala Lys
                85                  90                  95

Pro Ala Pro Cys Lys Pro Gly Thr Pro Val Leu Thr Gln Glu Met Val
            100                 105                 110

Ser Met Val Val Ser Thr Gly Gly Ser Ala Arg Val Ser His Asp Val
        115                 120                 125

Ala Pro Arg Phe Arg Val Gly Asp Trp Val Arg Thr Lys Asn Phe Asn
    130                 135                 140

Pro Thr Thr His Thr Arg Leu Pro Arg Tyr Ala Arg Asp Lys Val Gly
145                 150                 155                 160

Arg Ile Glu Ile Ala His Gly Val Phe Ile Thr Pro Asp Thr Ala Ala
        165                 170                 175

His Gly Leu Gly Glu His Pro Gln His Val Tyr Ser Val Ser Phe Thr
            180                 185                 190

Ala Gln Ala Leu Trp Gly Glu Pro Arg Pro Asp Lys Val Phe Ile Asp
        195                 200                 205

Leu Trp Asp Asp Tyr Leu Glu Glu Ala
210                 215

<210> SEQ ID NO 21
<211> LENGTH: 432
<212> TYPE: DNA
<213> ORGANISM: Brevibacterium linens, strain, 32B.1

<400> SEQUENCE: 21
atgaccgcca cctcggtccg agccgatacc acagaactcg gcgatgcacg ccgccgggtg      60
gagaaactcg tctgcagcct gcccggcgca ccgggcggtg acactgcgtt caccgcacca     120
tgggagatac gcgctttcgc cgatggcagtg gccgcctacg acgcacgcca gttcgaatgg     180
tccgaattcc agctctcctt gatcgagtcg atcaagtact gggaagaaaa cgaaggtgaa     240
tccgaacaga tcgtggtc gtactacgag cattggctta acgcgctcga aacccgcctg      300
tccgagagcg gactgctcag cgacgccgac ctcgacgagc gcaccacaac agtgctcgcc     360
accccgcccg atcgcgacca ccacaaagca cactcgaac cagtgagcat cgatcccgcc      420
cgcattcctt ag                                                         432

<210> SEQ ID NO 22
<211> LENGTH: 143
<212> TYPE: PRT
<213> ORGANISM: Brevibacterium linens, strain, 32B.1

<400> SEQUENCE: 22

Met Thr Ala Thr Ser Val Arg Ala Asp Thr Thr Glu Leu Gly Asp Ala
1               5                   10                  15

Arg Arg Arg Val Glu Lys Leu Val Cys Ser Leu Pro Gly Ala Pro Gly
            20                  25                  30

Gly Asp Thr Ala Phe Thr Ala Pro Trp Glu Ile Arg Ala Phe Ala Met
        35                  40                  45

Ala Val Ala Ala Tyr Asp Ala Arg Gln Phe Glu Trp Ser Glu Phe Gln
    50                  55                  60

Leu Ser Leu Ile Glu Ser Ile Lys Tyr Trp Glu Glu Asn Glu Gly Glu
65                  70                  75                  80

Ser Glu Gln Thr Ser Trp Ser Tyr Tyr Glu His Trp Leu Asn Ala Leu
                85                  90                  95

Glu Thr Arg Leu Ser Glu Ser Gly Leu Leu Ser Asp Ala Asp Leu Asp
            100                 105                 110

Glu Arg Thr Thr Thr Val Leu Ala Thr Pro Pro Asp Arg Asp His His
        115                 120                 125

Lys Ala His Leu Glu Pro Val Ser Ile Asp Pro Ala Arg Ile Pro
    130                 135                 140

<210> SEQ ID NO 23
<211> LENGTH: 6
<212> TYPE: PRT
<213> ORGANISM: Artificial Sequence
<220> FEATURE:

```
<223> OTHER INFORMATION: Description of Artificial Sequence: Motif of
      alpha-subunit

<400> SEQUENCE: 23

Phe Gly Leu His Ile Pro
1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Motif of
      alpha-subunit

<400> SEQUENCE: 24

Ser Glu Leu Ile
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Motif of
      alpha-subunit

<400> SEQUENCE: 25

Val Val Thr Ala Pro
1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Motif of
      alpha-subunit

<400> SEQUENCE: 26

Pro Ile Pro Thr
1

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Motif of
      alpha-subunit

<400> SEQUENCE: 27

Cys Lys Pro Gly Thr Pro
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Motif of
      alpha-subunit

<400> SEQUENCE: 28

Ser Met Val Val
1

<210> SEQ ID NO 29
```

-continued

```
<211> LENGTH: 4
<212> TYPE: PRT
<213> ORGANISM: Artificial Sequence
<220> FEATURE:
<223> OTHER INFORMATION: Description of Artificial Sequence: Motif of
      alpha-subunit

<400> SEQUENCE: 29

Glu Pro Arg Pro
1
```